United States Patent
Toor et al.

(10) Patent No.: US 12,421,266 B2
(45) Date of Patent: Sep. 23, 2025

(54) DIVERSE AND FLEXIBLE CHEMICAL MODIFICATION OF NUCLEIC ACIDS

(71) Applicant: The Regents of the University of California, Oakland, CA (US)

(72) Inventors: Navtej Toor, La Jolla, CA (US); Anastassia Hirlinger, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1214 days.

(21) Appl. No.: 17/278,432

(22) PCT Filed: Sep. 26, 2019

(86) PCT No.: PCT/US2019/053229
§ 371 (c)(1),
(2) Date: Mar. 22, 2021

(87) PCT Pub. No.: WO2020/069179
PCT Pub. Date: Apr. 2, 2020

(65) Prior Publication Data
US 2021/0347799 A1  Nov. 11, 2021

Related U.S. Application Data

(60) Provisional application No. 62/737,618, filed on Sep. 27, 2018.

(51) Int. Cl.
C07H 21/02 (2006.01)
C07H 1/00 (2006.01)
C07H 21/04 (2006.01)

(52) U.S. Cl.
CPC ............ *C07H 1/00* (2013.01); *C07H 21/02* (2013.01); *C07H 21/04* (2013.01)

(58) Field of Classification Search
None
See application file for complete search history.

(56) References Cited

U.S. PATENT DOCUMENTS

| | | |
|---|---|---|
| 2003/0215864 A1 | 11/2003 | Gilmanshin et al. |
| 2006/0063189 A1 | 3/2006 | Zon |
| 2006/0094678 A1 | 5/2006 | Vornlocher et al. |
| 2006/0223107 A1 | 10/2006 | Chenna et al. |
| 2015/0316482 A1 | 11/2015 | Natarajan et al. |

FOREIGN PATENT DOCUMENTS

WO   WO-2015060602 A1 *  4/2015  ........... C12N 15/115

OTHER PUBLICATIONS

International Search Report and Written Opinion dated Feb. 6, 2020, from application No. PCT/US2019/053229.

* cited by examiner

*Primary Examiner* — Traviss C McIntosh, III
(74) *Attorney, Agent, or Firm* — Foley & Lardner LLP

(57) ABSTRACT

The present invention provides a method for chemically modifying a nucleic acid molecule using sulfinate reagents to increase stability in vitro and in vivo. Screening methods for nucleobase modifications that reduce cleavage of a nucleic acid molecule by a nuclease are also provided.

10 Claims, 9 Drawing Sheets
Specification includes a Sequence Listing.

| Commercially Available Alkyne Labeled Lipids | Structure |
|---|---|
| Alkyne-cholesterol | 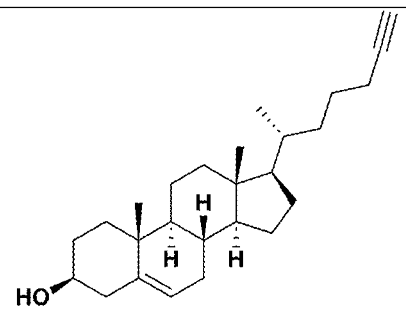 |
| 16:0(alkyne)-18:1 phosphoethanolamine | 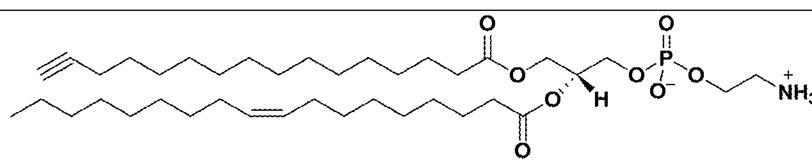 |
| pacFA ceramide | 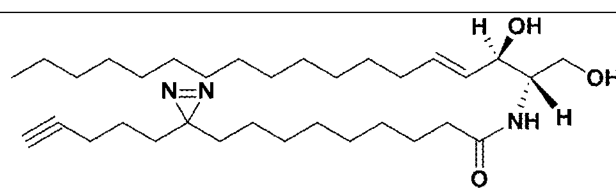 |

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
cagaatgctt aacgtccggt          20

<210> SEQ ID NO 2
<211> LENGTH: 20
<212> TYPE: DNA
<213> ORGANISM: Artificial Sequence
<220> FEATURE:
<223> OTHER INFORMATION: synthetic construct

<400> SEQUENCE: 2
cagaaugcuu aacguccggu          20

DIVERSE AND FLEXIBLE CHEMICAL MODIFICATION OF NUCLEIC ACIDS

CROSS REFERENCE TO RELATED APPLICATION(S)

This application is the U.S. National Stage Application under 35 U.S.C. § 371 of International Patent Application No. PCT/US2019/053229, filed Sep. 26, 2019, which claims the benefit of priority under 35 U.S.C. § 119 (e) of U.S. Ser. No. 62/737,618, filed Sep. 27, 2018, the entire content of each of which is incorporated herein by reference.

STATEMENT OF GOVERNMENT SUPPORT

This invention was made with government support under GM123275 awarded by the National Institutes of Health (NIH). The government has certain rights in the invention.

SEQUENCE LISTING

The instant applicant contains a Sequence Listing which has been submitted electronically in ASCII format and is hereby incorporate by reference in its entirety. Said ASCII, copy created on Mar. 19, 2021, is named 114198-5062_SL.txt and is 1 kilobyte in size.

BACKGROUND OF THE INVENTION

Field of the Invention

The invention relates generally to chemical modification of nucleic acid molecules, and more specifically to use of sulfinate reagents to modify C—H groups on heteroarenes to increase stability thereof and/or add functionality.

Background Information

Recently, there has been great success and interest in the use of RNA as a therapeutic for many different human diseases. Some of these RNA therapeutics have been FDA-approved and many others are currently in clinical trials. An example of a FDA-approved RNA therapeutic is Spinraza (generic name nusinersen), which is a chemically modified RNA that is used for the treatment of spinal muscular atrophy (SMA) (Claborn, M. K., Stevens, D. L., Walker, C. K. & Gildon, B. L. Nusinersen: A Treatment for Spinal Muscular Atrophy. Ann Pharmacother, 1060028018789956 (2018), incorporated herein by reference).

There are currently over 170 different RNA modifications that are known to exist in prokaryotes and eukaryotes. These RNA modifications affect all aspects of gene regulation and expression with effects upon both transcription and translation. The modifications occur on the nucleobase aromatic rings and are incorporated through the action of specific enzymes for each functional group that is added to the RNA. One of the most prevalent modifications is the presence of pseudouridine in mRNA, which greatly increases the half-life of pseudouridine-containing RNA by at least an order of magnitude as compared to unmodified RNA. Pseudouridine and its derivatives are now the basis for a multibillion-dollar industry that is now developing mRNA therapeutics for many diseases. mRNA can also be modified with other functional groups, such as N6-methyladenosine, to regulate its translation by the ribosome. Therefore, RNA modification is an emerging area of study that is revealing itself to be a significant mechanism for modulating biological pathways in the cell.

Even though RNA is showing great promise as a therapeutic, the synthesis and chemical diversity of modified RNA is limited by several known problems. Thus, there is a need for novel methods for chemically modifying nucleic acids (e.g., RNA) to increase in vivo stability for therapeutic purposes.

SUMMARY OF THE INVENTION

The present invention is based on the development of methodology for diverse and flexible chemical modification of nucleic acid molecules for increased stability, functional elucidation, and enhanced delivery of therapeutics. Accordingly, the invention provides a method of modifying a nucleic acid molecule. The method includes contacting the nucleic acid molecule with a sulfinate salt that includes an R functional group under conditions sufficient to add the R functional group on a Hoogsteen edge of a nucleobase of the nucleic acid molecule, thereby forming a modified nucleic acid molecule. In various embodiments, the contacting occurs in the presence of a radial initiator, such as tert-butyl hydroperoxide (TBHP).

In various embodiments, the nucleic acid molecule contains one or more heteroarene groups and the R functional group may be added to a C—H group on the one or more heteroarene groups. In various embodiments, the nucleobase is selected from the group consisting of adenine, deoxyadenine, guanine, deoxyguanine, 5-methyluracil, thymine, uracil, deoxyuracil, cytosine, deoxycytosine, and any combination or derivative thereof. In various embodiments, the nucleic acid molecule is selected from the group consisting of ribonucleic acid (RNA), deoxyribonucleic acid (DNA), threose nucleic acid (TNA), glycol nucleic acid (GNA), peptide nucleic acid (PNA), locked nucleic acid (LNA) and hybrids thereof. In various embodiments, the nucleic acid molecule is mRNA, an RNAi agent, siRNA, shRNA, miRNA, antisense RNA, ribozyme, or catalytic DNA. In various embodiments the nucleic acid molecule is either a small oligonucleotide, such as a 20-mer oligonucleotide or a large nucleic acid with a length of hundreds to thousands of nucleotides. In various embodiments, the sulfinate salt is selected from the group consisting of zinc trifluoromethanesulfinate (TFMS) and zinc bis(phenylsulfonylmethanesulfinate) (PSMS). In various embodiments, the percentage of nucleobases receiving the R functional group decreases with decreasing concentration of the sulfinate salt.

In another aspect, the invention provides a method of screening for nucleobase modifications that reduce cleavage of a nucleic acid molecule by a nuclease. The method includes contacting the nucleic acid molecule with a sulfinate salt comprising an R functional group under conditions sufficient to add the R functional group on a Hoogsteen edge of a nucleobase of the nucleic acid molecule, thereby forming a modified nucleic acid molecule, and monitoring degradation of the modified nucleic acid molecule over time in the presence of a nuclease, wherein decreased degradation in the presence of the nuclease, as compared to degradation in the presence of the nuclease of the nucleic acid molecule prior to modification is indicative of a R functional group that stabilizes the nucleic acid molecule. In various embodiments, the above-recited steps of contacting and monitoring may be repeated using an alkyne-labeled molecule that comprises a different R functional group for comparison to determine if one R function group confers increased stability of the nucleic acid molecule over the other.

In various embodiments, the nucleic acid molecule contains one or more heteroarene groups and the R functional group may be added to a C—H group on one or more heteroarene groups. In various embodiments, the nucleobase is selected from the group consisting of adenine, deoxyadenine, guanine, deoxyguanine, 5-methyluracil, thymine, uracil, deoxyuracil, cytosine, deoxycytosine, and any combination thereof. In various embodiments, the nucleic acid molecule is selected from the group consisting of RNA, DNA, TNA, GNA, PNA, LNA and hybrids thereof. In various embodiments, the nucleic acid molecule is mRNA, an RNAi agent, siRNA, shRNA, miRNA, antisense RNA, ribozyme, or catalytic DNA. In various embodiments the nucleic acid molecule is either a small oligonucleotide, such as a 20-mer oligonucleotide or a large nucleic acid with a length of hundreds to thousands of nucleotides.

In another aspect, the invention provides a method of modifying a nucleic acid molecule. The method includes contacting the nucleic acid molecule with an azide linker under conditions sufficient to add an azide group to a nucleobase of the nucleic acid molecule, thereby forming an azide-labeled nucleic acid molecule; and contacting the azide-labeled nucleic acid molecule with an alkyne-labeled molecule comprising an R functional group in the presence of a copper catalyst under conditions sufficient for covalent attachment of the R functional group to the nucleobase, thereby forming a modified nucleic acid molecule. In various embodiments, the nucleic acid molecule is contacted with an azide linker in the presence of a radial initiator, such as tert-butyl hydroperoxide (TBHP).

In various embodiments, the azide linker is a sulfinate salt that includes an azide group, such as (difluoroalkylazido) sulfinate (DAAS). In various embodiments, the copper catalyst is copper (I) that may be generated from copper (II) sulfate using ascorbate as a reducing agent. In various embodiments, the nucleic acid molecule contains one or more heteroarene groups and the R functional group may be added to a C—H group on the one or more heteroarene groups. In various embodiments, the nucleobase is selected from the group consisting of adenine, deoxyadenine, guanine, deoxyguanine, 5-methyluracil, thymine, uracil, deoxyuracil, cytosine, deoxycytosine, and any combination thereof. In various embodiments, the nucleic acid molecule is selected from the group consisting of RNA, DNA, TNA, GNA, PNA, LNA and hybrids thereof. In various embodiments, the nucleic acid molecule is mRNA, an RNAi agent, siRNA, shRNA, miRNA, antisense RNA, ribozyme, or catalytic DNA. In various embodiments the nucleic acid molecule is either a small oligonucleotide, such as a 20-mer oligonucleotide or a large nucleic acid with a length of hundreds to thousands of nucleotides.

In various embodiments, the R functional group includes a fluorophore. In various embodiments, the alkyne-labeled molecule is Fluor 488-alkyne. In various embodiments, the R functional group includes biotin, and the method may further include transfecting the biotinylated nucleic acid molecule into cells under conditions sufficient to allow for interaction with cellular protein cofactors, and thereafter, purifying the nucleic acid molecule with a streptavidin column to detect bound cellular proteins.

In various embodiments, the alkyne-labeled molecule is an alkyne-labeled lipid, such as, alkyne-cholesterol, 16:0 (alkyne)-18:1 phosphoethanolamine, or pacFA ceramide. In various embodiments, alkyne-labeled lipid also includes a fluorophore. In various embodiments, the percentage of nucleobases receiving the R functional group decreases with decreasing concentration of the sulfinate salt.

In another aspect, the invention provides a method of screening for nucleobase modifications that reduce cleavage of a nucleic acid molecule by a nuclease. The method includes contacting the nucleic acid molecule with an azide linker under conditions sufficient to add an azide group to a nucleobase of the nucleic acid molecule, thereby forming an azide-labeled nucleic acid molecule; contacting the azide-labeled nucleic acid molecule with an alkyne-labeled molecule comprising a R functional group in the presence of a copper catalyst under conditions sufficient for covalent attachment of the R functional group to the nucleobase, thereby forming a modified nucleic acid molecule; and monitoring degradation of the modified nucleic acid molecule over time in the presence of a nuclease, wherein decreased degradation in the presence of the nuclease, as compared to degradation in the presence of the nuclease of the nucleic acid molecule prior to modification is indicative of a R functional group that stabilizes the nucleic acid molecule. In various embodiments, the above-recited steps of contacting the nucleic acid molecule with an azide linker, contacting the azide-labeled nucleic acid molecule with an alkyne-labeled molecule and monitoring degradation of the modified nucleic acid molecule may be repeated using an alkyne-labeled molecule that comprises a different R functional group for comparison to determine if one R function group confers increased stability of the nucleic acid molecule over the other.

In various embodiments, the azide linker is a sulfinate salt that includes an azide group, such as (difluoroalkylazido) sulfinate (DAAS). In various embodiments, the copper catalyst is copper (I) that may be generated from copper (II) sulfate using ascorbate as a reducing agent. In various embodiments, the nucleic acid molecule contains one or more heteroarene groups and the R functional group may be added to a C—H group on one or more heteroarene groups. In various embodiments, the nucleobase is selected from the group consisting of adenine, deoxyadenine, guanine, deoxyguanine, 5-methyluracil, thymine, uracil, deoxyuracil, cytosine, deoxycytosine, and any combination thereof. In various embodiments, the nucleic acid molecule is selected from the group consisting of RNA, DNA, TNA, GNA, PNA, LNA and hybrids thereof. In various embodiments, the nucleic acid molecule is mRNA, an RNAi agent, siRNA, shRNA, miRNA, antisense RNA, ribozyme, or catalytic DNA. In various embodiments the nucleic acid molecule is either a small oligonucleotide, such as a 20-mer oligonucleotide or a large nucleic acid with a length of hundreds to thousands of nucleotides.

In another aspect, the invention provides a modified nucleic acid molecule as described herein.

DETAILED DESCRIPTION OF THE INVENTION

Figure 1:
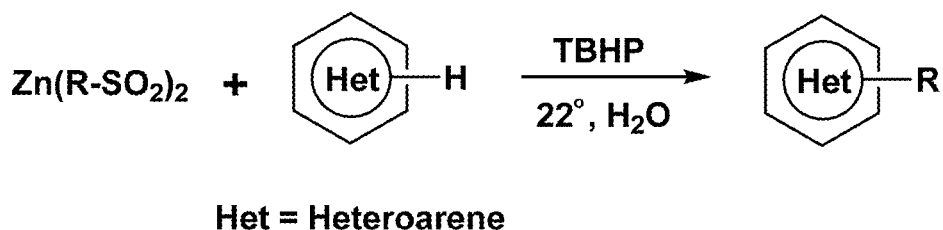
FIG. 1 is a pictorial diagram showing an exemplary chemical reaction for use of a zinc sulfinate salt to add an R group to the C—H position of a heteroarene. The R group can be varied to any desired function.

The present invention is based on the development of methodology for diverse and flexible chemical modification of nucleic acid molecules for increased stability, functional elucidation, and enhanced delivery of therapeutics.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "azide" refers to an anion with the formula $N_3^-$. As such, the term "azide group" refers to a compound having the general formula $RN_3$. "Azide reagents" or "azide linkers" can be used to react with alkyne-containing biomolecules.

As used herein, the term "heteroarene" refers to any heterocyclic compound derived from an arene by replacement of one or more methine and/or vinylene groups by trivalent or divalent heteroatoms respectively in such a way as to retain its aromaticity.

As used herein, the term "radical initiator" refers to any substance that can produce radical species under mild conditions and promote radical reactions. Exemplary radical initiators include, but are not limited to, halogen molecules, azo compounds (R—N=N—R'), and organic and inorganic peroxides.

As used herein, the term "tert-butyl hydroperoxide" (TBHP), having a preferred IUPAC name 2-methylpropane-2-peroxol, refers to an organic peroxide (i.e., radical initiator) widely used in a variety of oxidation processes.

As used herein, the term "nucleic acid," in its broadest sense, includes any compound and/or substance that is or can be incorporated into an oligonucleotide chain. In various embodiments the nucleic acid molecule is either a small oligonucleotide, such as a 20-mer oligonucleotide or a large nucleic acid with a length of hundreds to thousands of nucleotides. Exemplary nucleic acids for use in accordance with the present disclosure include, but are not limited to, one or more of ribonucleic acids (RNAs), deoxyribonucleic acids (DNAs), threose nucleic acids (TNAs), glycol nucleic acids (GNAs), peptide nucleic acids (PNAs), locked nucleic acids (LNAs) and hybrids thereof. In various embodiments, the nucleic acids used in accordance with the present disclosure include messenger mRNA (mRNA), RNAi-inducing agents, RNAi agents, siRNAs, shRNAs, miRNAs, antisense RNAs, ribozymes, catalytic DNA, RNAs that induce triple helix formation, aptamers, vectors, etc. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

As used herein "nucleoside" is defined as a compound containing a five-carbon sugar molecule (a pentose or ribose) or derivative thereof, and an organic base, purine or pyrimidine, or a derivative thereof. Exemplary nucleosides include, but are not limited to, adenosine, deoxyadenosine, guanosine, deoxyguanosine, 5-methyluridine, thymidine, uridine, deoxyuridine, cytidine, and deoxycytidine.

As used herein, "nucleotide" is defined as a nucleoside that includes a phosphate group. Thus, a nucleotide contains a nucleobase, a five-carbon sugar, and one or more phosphate groups.

As used herein, "nucleobase" refers to a nitrogen-containing biological compound that forms a nucleoside. The ability of nucleobases to form base pairs and to stack one upon another leads directly to long-chain helical structures such as RNA and DNA. The primary or canonical nucleobases that function as the fundamental units of the genetic code are adenine (A), cytosine (C), guanine (G), thymine (T), and uracil (U). Included in the term "nucleobase" are non-primary, modified and artificial nucleobases. Exemplary modified nucleobases include, but are not limited to, hypoxanthine, xanthine, 7-methylguanine, 5,6-dihydrouracil, 5-methylcytosine, 5-hydroxymthylcytosine, 2,6-diaminopurine, and 6,8-diaminopurine, and analogs or derivatives thereof. Exemplary artificial nucleobases include, but are not limited to, isoguanine, isocytosine, and analogs or derivatives thereof.

As used herein, the term "R group" refers to a series of one or more atoms that confers one or more specific chemical properties to the molecule to which it is attached. As used herein, the term "functional group" refers to a group of atoms responsible for the characteristic reactions of a particular compound.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

As used herein, "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process.

As used herein, "transcription factor" refers to a DNA-binding protein that regulates transcription of DNA into RNA, for example, by activation or repression of transcription. Some transcription factors effect regulation of transcription alone, while others act in concert with other proteins. Some transcription factors can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, viral DNA, and synthetic nucleic acids. A transcription termination sequence will usually be located 3' to the coding sequence.

As used herein, "Hoogsteen base pair" refers to a variation of base-pairing in nucleic acids such as the A.T pair. In this manner, two nucleobases, one on each strand, can be held together by hydrogen bonds in the major groove. A Hoogsteen base pair applies the N7 position of the purine base (as a hydrogen bond acceptor) and C6 amino group (as a donor), which bind the Watson-Crick (N3-C4) face of the pyrimidine base. In some DNA sequences, especially CA and TA dinucleotides, Hoogsteen base pairs exist as transient entities that are present in thermal equilibrium with standard Watson-Crick base pairs. The detection of the transient species required the use of NMR techniques that have only recently been applied to macromolecules.

As used herein, "click chemistry" refers to a class of biocompatible small molecule reactions commonly used in bioconjugation, allowing the joining of substrates of choice with specific biomolecules. "Click chemistry" is not a single specific reaction, but describes a way of generating products that follow examples in nature, which also generates substances by joining small modular units. In many applications, click reactions join a biomolecule and a reporter molecule. It should be understood that "click chemistry" is not limited to biological conditions: the concept of a "click" reaction has been used in pharmacological and various biomimetic applications. However, they have been made notably useful in the detection, localization and qualification of biomolecules.

As used herein, "unmodified" refers to a nucleic acid prior to being modified, e.g. adenosine, guanosine, cytosine, thymidine, and uracil, or a naturally occurring amino acid. The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

As used herein, "therapeutic agent" refers to any agent that, when administered to a subject, has a therapeutic, diagnostic, and/or prophylactic effect and/or elicits a desired biological and/or pharmacological effect.

As used herein, "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of a protein associated with a therapeutically active nucleic acid to a subject in need thereof.

As used herein, a "functional" biological molecule is a biological molecule in a form in which it exhibits a property and/or activity by which it is characterized.

As used herein, "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

As used herein, "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions.

As used herein, "biologically active" refers to a characteristic of any substance that has activity in a biological system and/or organism. For instance, a substance that, when administered to an organism, has a biological effect on that organism, is considered to be biologically active. In various embodiments, where a nucleic acid is biologically active, a portion of that nucleic acid that shares at least one biological activity of the whole nucleic acid is typically referred to as a "biologically active" portion.

As used herein, "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Endogenous chemical modifications of RNA play an essential role in both their stability and function in vivo. RNA can also be modified in vitro with other chemical groups to engineer additional functionality. For example, chemical modification of RNA therapeutics has been found to greatly enhance their stability and activity in treating human disease. Chemical modification is also used as a tool for solution probing of RNA structure and function. However, previous methods to modify RNA are extremely limited in terms of the diversity of the added functional groups and the high cost of synthesis. Reagents such as dimethyl sulfate and kethoxal have been historically used to modify the Watson-Crick edge of nucleobases in RNA for structure probing; however, it is not possible to add a variety of functional groups using this type of chemistry.

There currently are two principal methods to incorporate chemical modifications into synthetic RNAs: 1) short RNA oligonucleotides can be chemically synthesized to incorporate modifications; 2) in vitro transcription using T7 RNA polymerase in the presence of modified nucleoside triphosphates NTPs to generate modified long RNAs. However, both techniques have significant limitations that restrict either the length or the diversity of possible modifications. For example, T7 polymerase does not efficiently incorporate modified nucleobases during in vitro transcription. Long RNAs (>100 nucleotides) are typically synthesized using T7 RNA polymerase in the presence of modified nucleotide triphosphates (NTPs). However, T7 RNA polymerase is not able to accommodate highly modified NTPs within the restrictive confines of its active site. As a result, the diversity of modified RNA is limited by the enzymatic mechanism of T7 RNA polymerase. Further, the low efficiency of incorporation of modified NTPs during in vitro transcription results in exorbitant costs of synthesis. The limited number of modified NTPs that can be incorporated into RNA at low levels during synthesis results in very high costs of production. Modified NTPs are extremely expensive and the low efficiency of incorporation greatly increases the cost of synthesis for largescale production of therapeutics.

Accordingly, in one aspect, the present invention employs sulfinate chemistry to probe the structure of non-coding RNAs to overcome these two major obstacles to allow for the rapid, low-cost, and diverse chemical modification of RNAs of any size. Typical solution probing techniques for RNA interrogate either the ribose sugar or the Watson-Crick edge of some of the nucleobases. For example, SHAPE probing acylates the ribose sugar (12, 13), while other reagents such as dimethyl sulfate only target adenosine and cytidine with an alkyl group (6). These reagents are very limited in terms of the diversity of RNA modifications. In addition, current techniques only probe the ribose sugar and the Watson-Crick edge of nucleobases. They provide insight into secondary structure, but not the three-dimensional (3D) local structure of the RNA.

Accordingly, the present invention provides methodology that allows for the addition of any desired functional group to all four nucleobases of a nucleic acid molecule with high yields. This allows for the exploration and development of tools that is applicable to the entire universe of RNA chemical space. The invention therefore provides methods for generating nucleic acid molecules that exhibit stability against nucleases, methods for functionalizing nucleic acid molecules to be highly efficient in transfection across cell membranes for therapeutic purposes, and methods for covalent attachment of fluorophores to any nucleic acid sequence for tracking within cells.

As demonstrated herein, sulfinate chemistry has been adapted to introduce any desired chemical modification into a nucleic acid molecule (e.g., RNA). The sulfinate reagents modify the Hoogsteen edge of all four nucleobases and therefore give unique insight into RNA structure since the Hoogsteen edge plays a crucial role in formation of tertiary contacts and base triples in structured RNAs (14). Furthermore, the R group attached to the sulfinate salt can be modified to have different biophysical properties that result in different modification patterns according to the target RNA structure. In this regard, it has been found that altering the hydrophobicity of the R group results in drastically different modification patterns that correspond to different structures within the RNA.

As such, the techniques described herein involve post-transcriptionally modifying the RNA using a sulfinate salt with any desired R functional group. This results in the modification of the C—H groups on the aromatic rings of the nucleobases. The degree of modification of the RNA can be modulated by varying the concentration of the sulfinate salt and/or TBHP. This allows for the addition of any functional group (i.e., R group) to RNA from an entire universe of possible modifications. Because this reaction is done after in vitro transcription of the RNA, the limitations imposed by T7 RNA polymerase are bypassed.

Exemplary sulfinate salts useful in the reactions of the methods described herein include, but are not limited to, zinc sulfinate salts such as zinc bis(phenylsulfonylmethanesulfinate) (PSMS), zinc (trifluoromethanesulfinate) (TFMS), zinc benzylsulfinate, zinc bis[(phenylsulfonyl)methanesulfinate], zinc chloroethanesulfinate, zinc chloromethanesulfinate, zinc isopropylsulfinate, zinc n-propylsulfinate, zinc difluoromethanesulfinate, zinc trifluoroethanesulfinate, and zinc trifluoromethanesulfinate; sodium sulfinate salts such as sodium N-benzyloxycarbonyl-4-piperidinesulfinate, sodium 2-(4-Bromophenyl)-1,1-difluoroethanesulfinate, sodium (4-bromophenyl)methanesulfinate, sodium tert-butylsulfinate, sodium 7-Chloro-1,1-difluoroheptane-1-sulfinate, sodium 7-(ethylthio)-1,1-difluoroheptane-1-sulfinate, sodium (4-chlorophenyl)methanesulfinate, sodium (2,4-dichlorophenyl)methanesulfinate, sodium 2,2-dimethylpropylsulfinate, sodium ethylsulfinate, sodium isopropylsulfinate, sodium (4-methoxyphenyl)methanesulfinate, sodium 4-Methyl-benzenemethanesulfinate, sodium 2-Naphthalenemethanesulfinate, sodium 1-Phenoxy-methanesulfinate, sodium propane-l-sulfinate, sodium difluoroheptylazidosulfinate, sodium 1,1-difluoro-4-(2-methyl-1,3-dioxolan-2-yl)butane-1-sulfinate, sodium cyclohexanesulfinate, sodium 2-methylcyclopropylsulfinate, sodium 2-(3-oxetane)propylsulfinate, sodium phenylmethanesulfinate, sodium tetrahydrofuransulfinate, sodium tetrahydropyransulfinate, sodium 1,1-difluoroethanesulfinate, sodium trifluoropropylsulfinate, sodium 4,4-difluorocyclohexanesulfinate, and sodium 1-(trifluoromethyl)cyclopropanesulfinate; and azide sulfinate salts such as (difluoroalkylazido)sulfinate (DAAS).

Accordingly, the invention provides a method of modifying a nucleic acid molecule. The method includes contacting the nucleic acid molecule with a sulfinate salt, such as zinc sulfinate salt, that includes an R functional group under conditions sufficient to add the R functional group on a Hoogsteen edge of a nucleobase of the nucleic acid molecule, thereby forming a modified nucleic acid molecule. Nucleic acids for use in accordance with the present disclosure may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) Oligonucleotide synthesis: a practical approach, Oxford [Oxfordshire], Washington, D.C.: IRL Press, 1984; and Herdewijn, P. (ed.) Oligonucleotide synthesis: methods and applications, Methods in Molecular Biology, v. 288 (Clifton, N.J.) Totowa, N.J.: Humana Press, 2005; both of which are incorporated herein by reference).

In various embodiments, the method for modifying the nucleic acid molecule may be used to build a database that would correlate percent modification using different R group sulfinate salts and the corresponding RNA structure. This provides the ability to determine the fine fingerprint of specific RNA structural motifs using sulfinate chemistry, as well as allow for the accurate determination of the solution structure of any given non-coding RNA. In addition, this analysis will also provide for the characterization of the type and level of modification of RNA under different conditions. To accomplish this goal, initial zinc sulfinate probing of model RNAs, such as the group II intron of *Oceanobacillus iheyensis* (O.i.) and a ribosome will be performed. The probed data will be mapped onto the local 3D RNA structure to build a database of modification patterns correlated to specific classes of RNA structural motifs. The end goal is that this would allow one to use this methodology and database to gain structural insight into any RNA of interest, as well as characterize the modification properties of a given zinc sulfinate reagent. This is impactful since RNA structure is closely correlated to its function in biology.

As such, the present invention provides polynucleotide libraries containing nucleoside modifications, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide. In various embodiments, multiple variants of a protein, each with different amino acid modification(s), are produced and tested to determine the best variant in terms of pharmacokinetics, stability, biocompatibility, and/or biological activity, or a biophysical property such as expression level.

Sulfinate Chemistry Applied to RNA

As discussed above, the present invention allows for the addition of any desired functional group to carbon-hydrogen (C—H) sites found on all four nucleobases of RNA. This was accomplished through the adaptation of sulfinate chemistry to modify RNA. As shown in exemplary FIG. 1, zinc sulfinate was used to modify nitrogen-rich aromatic rings (heteroarenes) through the formation of C—C bonds at a C—H position in a target molecule. This reaction is done under very mild conditions in the absence of harsh solvents. The zinc sulfinate salt can be synthesized with any desired R functional group, thereby allowing diverse modifications to be added to RNA.

Figure 2:
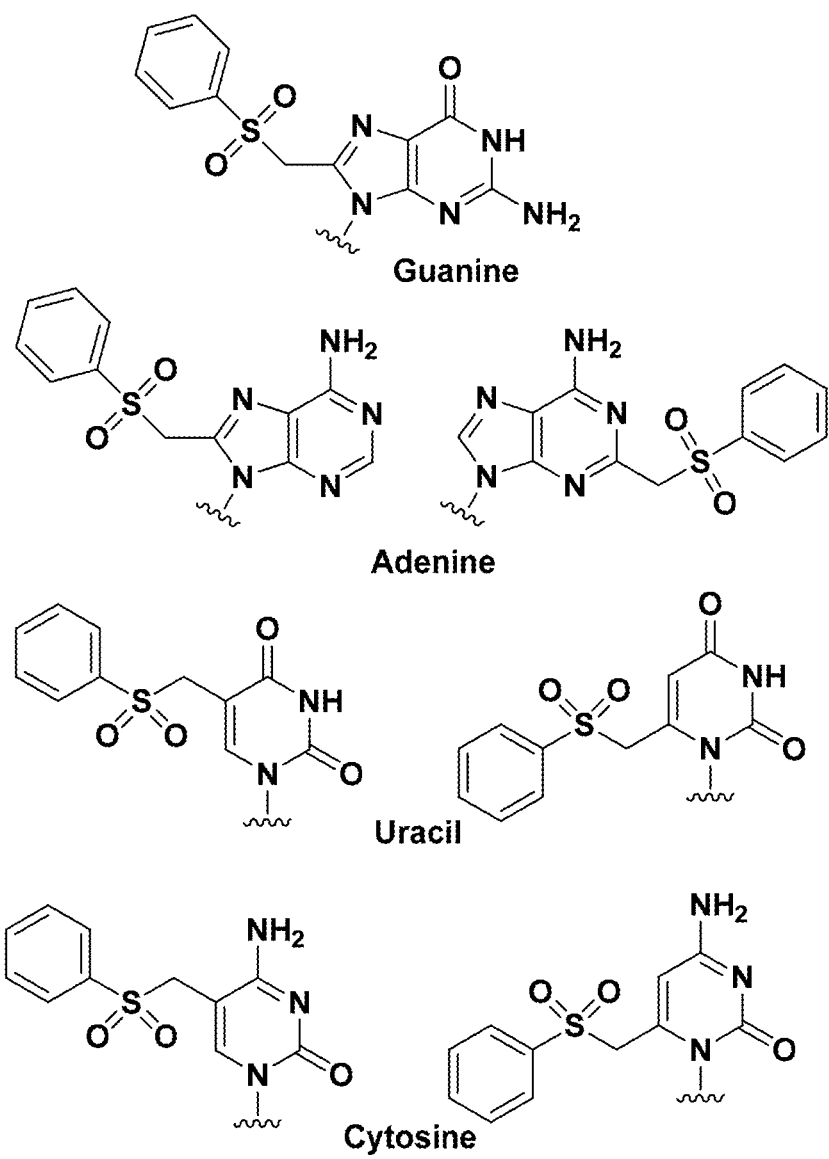
FIG. 2 is a pictorial diagram showing that zinc bis (phenylsulfonylmethanesulfinate) (PSMS) can modify all four nucleobases with an R group containing a phenyl ring. This R group is added to the Hoogsteen edge of each base. Adenine is the only exception in that it does have a possible site on the Watson-Crick edge.

As part of the preliminary studies, two different zinc sulfinate reagents were used to modify a 388-nucleotide group II intron RNA as a test molecule. Zinc bis(phenylsulfonylmethanesulfinate) (PSMS) is capable of attaching a phenylsulfonylmethyl modification to C—H groups on all four nucleobases of RNA, while zinc (trifluoromethanesulfinate) (TFMS) attaches a $CF_3$ group (FIG. 2). This R group can be varied to any desired functional group therefore allowing one to explore an infinite chemical space, such as for optimizing RNA therapeutics. PSMS and TFMS were selected as reagents for these pilot studies to modify RNA since they represent extremes of size with PSMS adding a very bulky phenyl group and TFMS adding the small $CF_3$ group.

Figure 3:
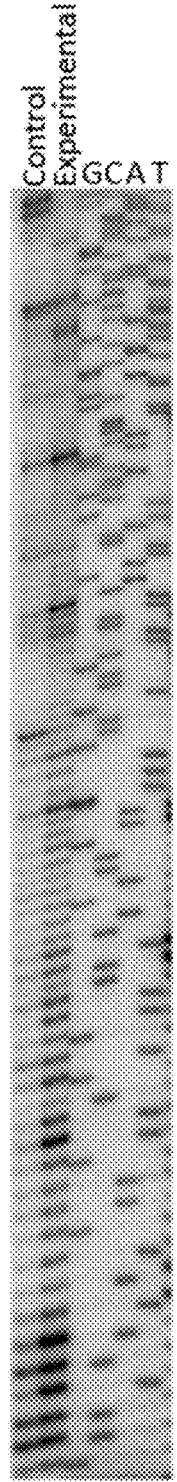
FIG. 3 is a pictorial diagram showing the results from primer extension using a reverse transcriptase to reveal the location of chemical modifications on the RNA. Experimental lane shows extra bands compared to the control lane. These additional bands are the sites of modification. Correlation with the GCAT sequencing ladder indicates the nucleotide identity of the site of modification.

Thus, in exemplary embodiments, the methodology may first involve synthesizing the RNA using in vitro transcription, followed by post-transcriptional modification of the RNA using a zinc sulfinate reagent. A group II intron RNA was selected for the initial zinc sulfinate reactions as it is highly structured and would likely provide a greater hurdle for modification. As shown in FIG. 3, the sites of modification using PSMS are detected as primer extension stops using reverse transcriptase. A modified nucleotide will prevent the reverse transcriptase from continuing and results in a stop that appears as a band in the sequencing gel. This experiment shows that the zinc sulfinate modification results in a distinct modification pattern that is consistent with the addition of functional group to all four nucleobases of RNA.

Probing RNA Structure Using Sulfinate Reagents

Figure 4A:
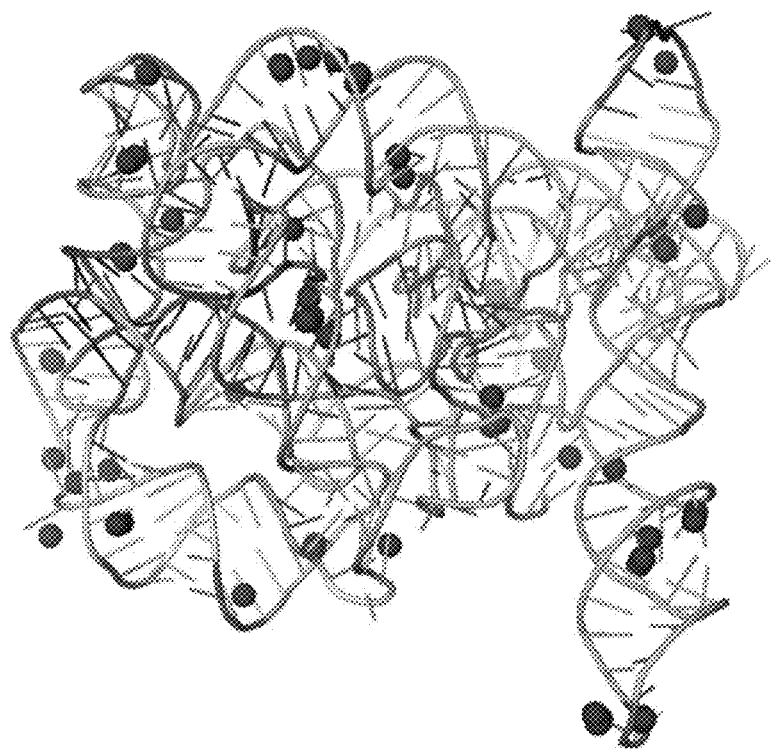
FIGS. 4A and 4B are pictorial diagrams showing a comparison of the sites of chemical modification by PSMS (FIG. 4A) and TFMS (FIG. 4B) mapped onto the 3D structure of the O.i. group II intron (PDB 3IGI). These zinc sulfinate reagents exhibit different patterns of modification. They likely interrogate different aspects of the RNA structure.
Figure 4B:
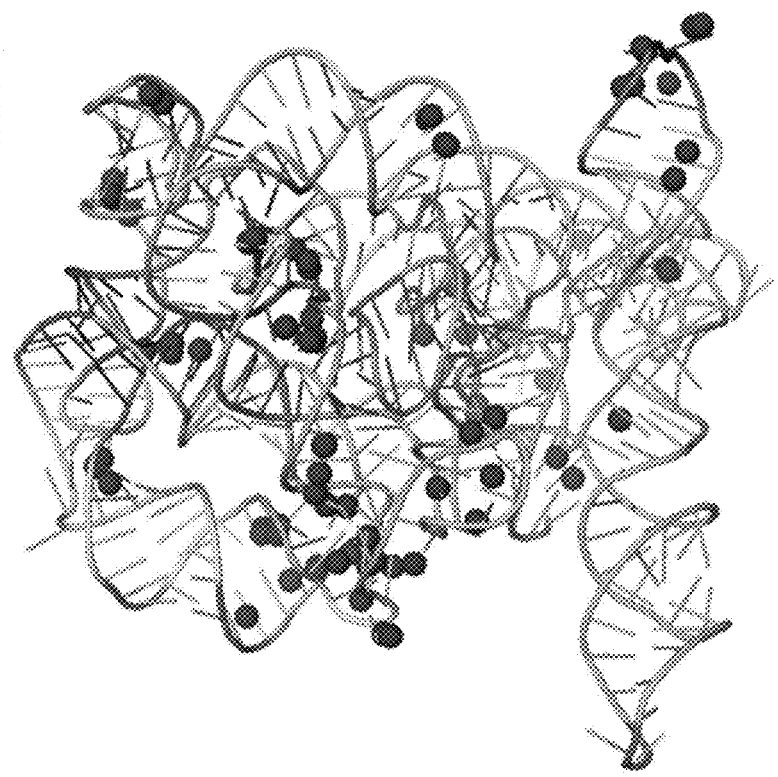

The sites of sulfinate modification on *Oceanobacillus iheyensis* (O.i.) group II intron RNA were compared using both TFMS and PSMS. These sites were mapped onto the 3D structure to reveal that each reagent has a unique pattern of modification (see FIGS. 4A and 4B). Without being bound by theory, these reagents are likely interrogating different structural features of the RNA due to the contrasting biophysical properties of the polar $CF_3$ group compared to the hydrophobic phenyl ring having different binding characteristics to the RNA.

This showed that both TFMS and PSMS have very different modification patterns for the O.i. group II intron. Typical structure probing techniques such as SHAPE and DMS are only able to modify single-stranded flexible regions of the RNA. In contrast, the sulfinate salts have specific regions of modification that cover both single-stranded and helical regions. High modification in regions containing non-canonical pairs that have a distorted helical geometry in the corresponding 3D structure were observed. Therefore, targeting the Hoogsteen edge of nucleotides gives new insight into the solution structure of RNA beyond just simple secondary structure. As a result, this opens up the possibility to identify local 3D RNA structure that is not amenable to identification by current chemical methods.

Correlation of Sulfinate Modification and RNA Structure

In order to determine the precise relationship between modification and local RNA structure, we will first obtain zinc sulfinate probing data for the two group II introns, as well as the large ribosomal unit from *Haloarcula marismortui* (H.m.) (18). All probing reactions will be done in triplicate and the resulting sites of modification mapped onto the 3D structures. Computational tools will then be used to determine the local geometry of the modified sites on the RNA using $\eta$-$\theta$ plots, which are pseudotorsion angles that allow for the identification of specific RNA structural motifs (19, 20). These are analogous to the $\varphi$-$\Psi$ angles that are used to identify protein secondary structure using Ramachandran plots. The goal is to determine values of $\eta$-$\theta$ that identify RNA structures targeted by a specific zinc sulfinate reagent. For example, this analysis may identify helical geometry more likely to open up the Hoogsteen edge of nucleobases to attack by a given zinc sulfinate reagent with a specific R functional group. Furthermore, changing the identity of the R group on the zinc sulfinate salt will likely lead to the interrogation of different RNA structures as seen with the comparison between PSMS and TFMS.

The modification patterns for these zinc sulfinate salts will be directly compared with the standard techniques for RNA secondary structure probing that use dimethyl sulfate (DMS), kethoxal, and SHAPE. These standard reagents will be used to generate a comparative dataset of the aforementioned model RNAs.

Nuclear Magnetic Resonance (NMR) and Primer Extension to Verify Modification of RNA To get a direct biophysical readout of successful modification of the RNA by the zinc sulfinate reagent, both NMR and primer extension were used to verify the addition of the $CF_3$ group by TFMS. The TFMS modified RNA was analyzed by F-19 NMR and this showed the presence of two peaks between −61 and −62 ppm, which is consistent with the chemical shift range for the $CF_3$ group attached to a nitrogen-containing aromatic ring (see FIG. 12) (15). The double peak pattern likely results from the different nucleobases slightly altering the chemical shift of $CF_3$. In contrast, the peak for the pure TFMS salt is at −87 ppm. Therefore, the NMR data is consistent with modification of the RNA by the TFMS reagent. Taken together, the primer extension data and NMR data support successful modification of the RNA by the zinc sulfinate reagents. This is also consistent with the known ability of zinc sulfinate reagents to modify C—H groups on aromatic rings. Given the versatility of the zinc sulfinate chemistry, this opens up the possibility of adding any desired functional group to RNA.

Determine Structural Basis of Sulfinate Modification of Model RNAs

The data so obtained may then be used to determine the high-resolution crystal structures of the two group II introns analyzed above in order to visualize the modified nucleobases in the various pockets of the RNA structure. The goal is to determine the structural basis for the modification of specific sites in the RNA by the zinc sulfinate salt. Observation of how certain highly modified regions of the RNA are able to react with the zinc sulfinate salt is expected. This will be done on the group II intron RNAs both in solution as well as in crystallo. RNA crystals will be soaked in the zinc sulfinate salt for modification and then the structures will be determined using x-ray crystallography. This crystallized RNA will also be used for detection of sites using primer extension assays (as described herein) and the two datasets will be compared. These sites of modification can be easily visualized at 3 angstroms resolution using Fo-Fc omit maps.

Introduction of Click Chemistry Functional Groups into Long RNAs

As described above, the adaption of sulfinate chemistry allows for the addition of any desired chemical group, thereby increasing the functionality of RNA. However, each R group requires the synthesis of a new zinc sulfinate reagent, and therefore, high-throughput screening of R functional groups for a desired activity can be expensive in terms of time and money. To circumvent this problem, the present invention provides for use of a sulfinate salt that adds an azide group to the nucleobase of RNA, which would serve as point of attachment for copper-click chemistry reactions with an alkyne-labeled molecule. Copper-catalyzed click chemistry involves the formation of a covalent bond between an alkyne and an azide group under mild conditions. There are numerous commercially available compounds that are labeled with alkyne groups for click chemistry.

Accordingly, in another aspect, the invention provides a method of modifying a nucleic acid molecule. The method includes contacting the nucleic acid molecule with an azide linker under conditions sufficient to add an azide group to a nucleobase of the nucleic acid molecule, thereby forming an azide-labeled nucleic acid molecule; and contacting the azide-labeled nucleic acid molecule with an alkyne-labeled molecule comprising an R functional group in the presence of a copper catalyst under conditions sufficient for covalent attachment of the R functional group to the nucleobase, thereby forming a modified nucleic acid molecule.

Rapid, One-Step Attachment of Diverse Fluorophores to Long RNAs

Fluorescent labeling of nucleic acids is an essential tool for studying the structure and function of RNAs in vivo. Fluorescent labeling of long RNAs is typically done using a MS2 coat protein fused with fluorescent GFP (MS2-GFP) that binds engineered stem loop structures within the target RNA. This association between the RNA and the protein is noncovalent and is also labor intensive. Determining the positions of the engineered MS2-binding stem loops within the target RNA requires trial and error as there are no known rules for successful incorporation (21). Also, the addition of multiple stem loops is required to obtain sufficient fluorescent signal, however, this large addition of sequence could also disrupt the function of the native RNA (21). In addition, aggregation of RNA-free MS2-GFP protein can also result in artefacts during cellular imaging. Thus, the present invention provides a technique that allows for the low-cost, covalent addition of fluorophores to a wild-type target RNA of any sequence without the need for incorporating engineered stem loops.

In various embodiments, the methods provided herein utilize a sulfinate salt to add an azide group to RNA nucleobases. This azide-labeled RNA may be reacted with an alkyne-labeled fluorescent dye to allow for efficient fluorescent labeling. The resulting fluorescent RNA may be used for in vivo studies to track non-coding RNA within cells. Accordingly, this scheme will provide for the following added functionality for RNA: 1) fluorescent labeling of RNA; 2) generation of covalent lipid-RNA conjugates that efficiently cross the cell membrane for therapeutic use; and 3) identification of functional groups that increase mRNA stability through resistance to nucleases. All of these modifications occur on the Hoogsteen edge of the nucleobase and therefore are not expected to significantly affect the Watson-Crick pairing potential of the modified RNA.

Figure 5:
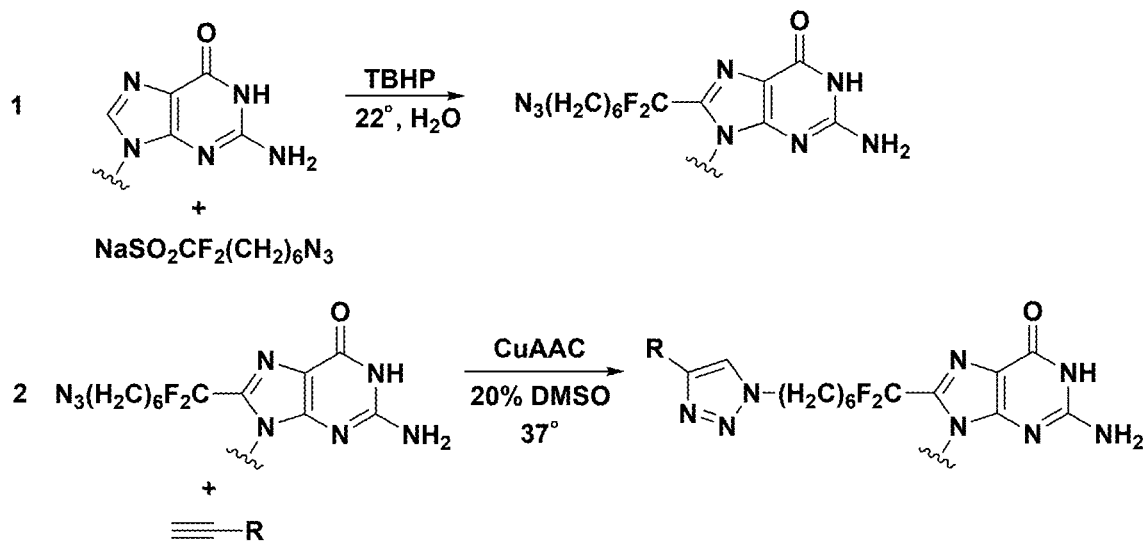
FIG. 5 is a pictorial diagram showing an exemplary chemical reaction for combining sulfinate chemistry with click ligation. In the first step, the nucleobase is labeled with an azide group using the DAAS-Na reagent (top panel). This is followed by a click chemistry reaction using an alkyne-labeled reagent containing an R functional group.

Sodium (difluoroalkylazido)sulfinate (DAAS-Na) is an exemplary sulfinate reagent that adds an azide group to an heteroarene C-H. This will be reacted with RNA to form nucleobases labeled with an azide group (FIG. 5). This azide group then allows for reaction with an alkyne-labeled molecule (23, 24) to result in covalent addition of a functional group to the RNA nucleobase. This method does not require synthesis of a new sulfinate salt for a specific R group. Instead, the azide-labeled RNA is generated once and then can be subdivided into aliquots for reactions with different alkyne-labeled reagents to generate RNAs with diverse functionalities. This allows rapid screening of functional groups for a desired RNA property.

Figure 14A:
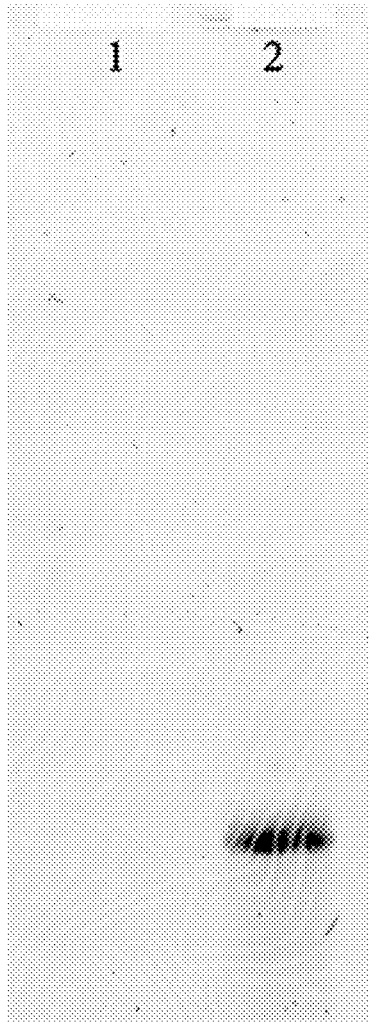
FIGS. 14A and 14B are pictorial diagrams showing the results from fluorophore-labeled O.i. RNA on 4% acrylamide denaturing PAGE gel using a GE Typhoon Fluorescent Image Analyzer Scanner with a 473 nm excitation beam and an LPB filter (FIG. 14A), and the same UV-illuminated gel stained with ethidium bromide (FIG. 14B).

Initial studies involved reacting an alkyne-labeled fluorophore called Fluor 488-alkyne with an azide-labeled group II intron to form RNA covalently attached to this dye. First, the O.i. group II intron was reacted with DAAS-Na to generate azide-labeled RNA. This modification was verified through primer extension (data not shown). Next, the modified RNA was reacted with Fluor 488-alkyne in the presence of a copper catalyst for the click chemistry reaction (FIG. 5). The control consisted of unlabeled RNA incubated with Fluor 488-alkyne alone. Both the experimental and control RNAs were thoroughly washed through diafiltration with seven changes of buffer to ensure that unbound dye was removed from the samples. These RNAs were resolved on a 4% denaturing polyacrylamide gel and visualized using a Typhoon imager in fluorescence mode at 473 nm wavelength. This revealed that the RNA was successfully labeled with Fluor 488 as evidenced by the detection of a strong fluorescent band corresponding to the expected size of the RNA according to migration on the gel (FIG. 14A).

Figure 14B:
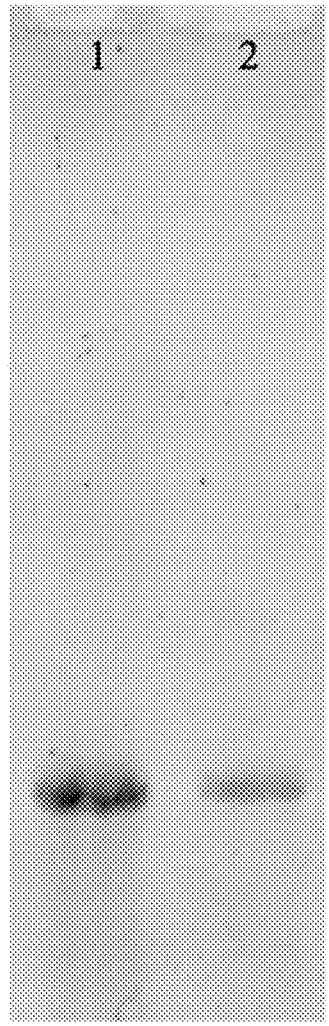

In contrast, the control RNA incubated with dye showed no fluorescence signal as expected. Both the control and experimental lanes were shown to contain RNA through ethidium bromide staining and visualization with UV light (FIG. 14B). Therefore, this data shows that any long RNA can be covalently labeled with a fluorophore using a combination of sulfinate and copper click chemistry. Further optimization will be done to ensure that the level of modification is appropriate to retain the biological activity of the RNA, while maximizing the fluorescent signal.

In Vivo Imaging of Fluorescent RNA

To test the utility of this tool in tracking RNAs in vivo, the long non-coding RNA (lncRNA) MALAT1 with Fluor 488 will be fluorescently labeled. MALAT1 is a model lncRNA that is expressed in many cancers and is also important for development (25, 26). Furthermore, MALAT1 has a characteristic localization pattern within cells that can be easily identified (27). This fluorophore-containing MALAT1 RNA will be transfected into 293T cells in tissue culture and the localization of the fluorescent RNA within the cell monitored using microscopy. MALAT 1 has a well-defined localization pattern within cells, which will enable assessment of the fluorescent signal. The signal strength and localization of Fluor 488-labeled RNA will be directly compared with that obtained for RNA attached to the fluorescent MS2 coat protein. The MS2-GFP fusion construct is typically used for RNA localization studies in live cells. This method of covalently labeling a long RNA should give a significantly stronger signal and greater sensitivity compared to typical approaches using fluorescent MS2 coat protein.

Accordingly, in another aspect, the invention provides a method of screening for nucleobase modifications that reduce cleavage of a nucleic acid molecule by a nuclease. The method includes contacting the nucleic acid molecule with an azide linker under conditions sufficient to add an azide group to a nucleobase of the nucleic acid molecule, thereby forming an azide-labeled nucleic acid molecule; contacting the azide-labeled nucleic acid molecule with an alkyne-labeled molecule comprising a R functional group in the presence of a copper catalyst under conditions sufficient for covalent attachment of the R functional group to the nucleobase, thereby forming a R functional group modified nucleic acid molecule; and monitoring degradation of the modified nucleic acid molecule over time in the presence of a nuclease, wherein decreased degradation in the presence of the nuclease, as compared to degradation in the presence of the nuclease of the nucleic acid molecule prior to modification is indicative of a R functional group that stabilizes the nucleic acid molecule.

Modulating the Extent of Labeling

The percentage of modified nucleotides can be adjusted through variation of the concentration of the sulfinate salt during the labeling reaction. It is therefore possible to reduce the number of modifications to ~1 per RNA with a reduction of the zinc sulfinate concentration. This is important because it is desirable to keep as much of the RNA in a native condition to preserve its biological activity. Thus, the percentage of nucleobases receiving the R functional group decreases with decreasing concentration of the sulfinate salt.

Identifying Covalent Lipid-RNA Conjugates to Allow Efficient Transfection

Using RNA as a therapeutic requires that it cross the lipid cell membrane. Recently, it has been found that chemical synthesis of short siRNAs conjugated at the 5' end to lipid groups allows efficient delivery to the cells of different organs and tissues (29). This work showed that the addition of a single lipid group to an siRNA was sufficient to allow efficient transfection of cells. However, this existing technique is restricted to small RNAs with the chemical synthesis of lipid-conjugated RNAs being very expensive and time-consuming. Therefore, this limits the number of lipids that can be rapidly screened for efficient delivery to cells.

Figure 6:
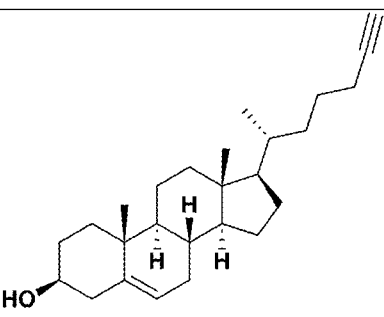
FIG. 6 is a chart showing a partial listing of the some of the commercially available lipids that will be conjugated to RNA for efficient transfection of nucleic acids across the cellular membrane.
Figure 6:
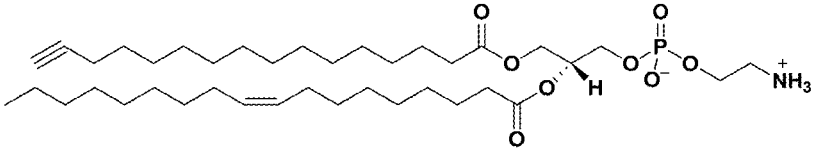
Figure 6:
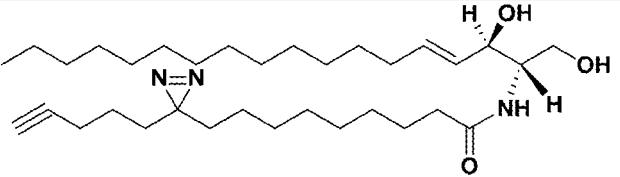

A library of alkyne-labeled lipids will be reacted with azide-labeled RNA and tested in a mouse model for efficiency of transfection. This would allow rapid and high-throughput screening of lipid groups that would enable high-efficiency transfection of cells. The goal is to find specific lipid-RNA conjugates that maximize delivery for therapeutic purposes. FIG. 6 provides a subset of exemplary alkyne-labeled lipids that may be attached to the azide-labeled RNA. For in vivo studies in tissue culture, the RNA may be labeled with both lipids and a fluorophore simultaneously. This will allow for fluorescent imaging to track the location and spread of a given lipid-RNA conjugate. The lipid-RNA conjugate showing the highest efficiency of transfection will be selected for further development and modification. Transfection efficiency will be monitored through detection of fluorescence. As discussed above, the level of modification can be tailored through adjustment of the DAAS-Na concentration to ensure that excessive labeling of the RNA does not occur.

Development of Biotin Labeling for RNA

The mechanism of action of lncRNAs is a topic of great interest since such nucleic acid molecules may be effective as a vaccine when administered to a mammalian subject. Such modified nucleic acids are generally not translated but are capable of binding to and sequestering one or more translational machinery components such as a ribosomal protein or a transfer RNA (tRNA), thereby effectively reducing protein expression in the cell. The modified nucleic acid may be a small nucleolar RNA (sno-RNA), micro RNA (miRNA), small interfering RNA (siRNA) or Piwi-interacting RNA (piRNA).

It is thought that these non-coding RNAs bind to multiple proteins that play a major role in their function (30). Therefore, the identification of these proteins would give insight into how non-coding RNAs affect the cell. This can be done through biotin labeling of the RNA followed by streptavidin purification to pull down the RNA with its bound proteins. Mass spectrometry could then be used to identify the attached proteins. Therefore, efficient biotin labeling of RNA has been a desired tool for many years. It is possible to use 3' biotin labeling of RNA (31), however this requires enzymatic addition that is relatively laborious and may not be efficient due to local secondary structure.

Figure 7:
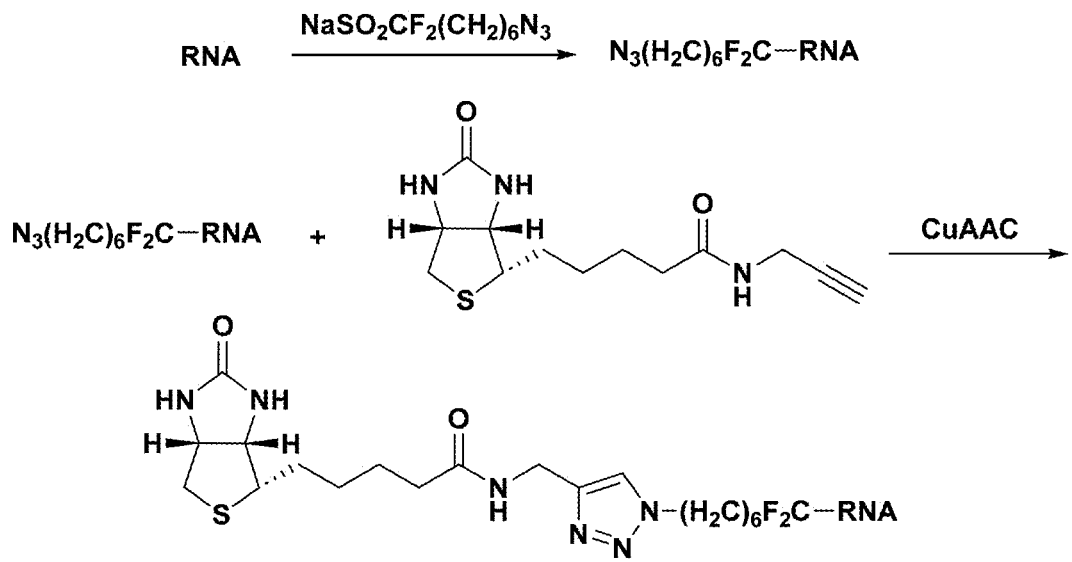
FIG. 7 is a pictorial diagram showing an exemplary chemical reaction of azide-labeled RNA reacted with biotin-alkyne to yield biotin-labeled RNA.

Accordingly, the present invention may be used to react biotin-alkyne with the azide-labeled RNA to generate biotinylated RNA (FIG. 7). The level of biotinylation will be adjusted through variation of the DAAS-Na concentration during the modification reaction. This biotinylated RNA can be transfected into cells and allowed to interact with cellular protein cofactors followed by streptavidin column purification and mass spectrometry. This would allow rapid and low-cost biotin labeling of RNA and greatly facilitate the identification of bound proteins to elucidate the mechanism of action of lncRNAs.

Stabilization of RNA to Increase its Half-Life for Therapeutic Use

RNA is prone to degradation and has a relatively short half-life within the cell, which limits its effectiveness as a therapeutic. Recently, it has been found that the introduction of modified nucleotides into mRNA can greatly increase the half-life by more than an order of magnitude (1, 2, 32). However, these modifications are typically incorporated during in vitro transcription by T7 RNA polymerase, which is highly restricted in accommodating modified nucleotide triphosphates within the confines of its active site. As a result, relatively few modifications have been identified to improve the half-life of RNA. One of the most widely used modifications is the incorporation of pseudouridine to completely substitute for uridine. Pseudouridine has been shown to increase the half-life of mRNA to 3 days, as compared to unmodified RNA that has a half-life of only a few hours (1, 2, 32). Therefore, modification of nucleobases can greatly improve the stability of RNA.

The present invention may therefore be used to attach a wide variety of alkyne-labeled compounds to the azide-labeled nucleobases of RNA with the purpose of stabilizing the molecule against nuclease-mediated degradation. Nucleases such as RNase A and T1 have sequence specificity in their cleavage patterns. RNase A cleaves the 3' ends of C and U residues, while RNase T1 cleaves on the 3' end of G nucleotides (7). It is therefore contemplated that modifying the nucleobases with non-natural modifications using a combination of sulfinate and click chemistry will render these RNAs resistant to nuclease cleavage. It has previously been found that nucleobase modifications can reduce cleavage of RNA by nucleases (33). This in vitro assay will involve testing each modification with RNase A and T1 and monitoring the level of degradation over time on a denaturing polyacrylamide gel. The goal is to identify a functional group that will stabilize the RNA and prevent cleavage by these and other nucleases. Incorporation of these modifications into RNA therapeutics will greatly increase the half-life of these molecules in vivo. As such, the present invention greatly expands the chemical space of RNA functionality and will have a paradigm-shifting impact upon the development of nucleic acid therapeutics.

In various embodiments, the modified nucleic acid exhibits reduced degradation in a cell into which the nucleic acid is introduced, relative to a corresponding unmodified nucleic acid. Exemplary nucleic acids include ribonucleic acids (RNAs), deoxyribonucleic acids (DNAs), threose nucleic acids (TNAs), glycol nucleic acids (GNAs), locked nucleic acids (LNAs) or any hybrid thereof.

As demonstrated herein, the present invention incorporates organic chemistry to modify in vitro transcribed RNA post-transcriptionally. In various embodiments, RNA may be first synthesized using T7 RNA polymerase and then the RNA is modified using zinc sulfinate chemistry. Zinc sulfinate reagents are able to modify C—H groups on heteroarenes to attach any given R group (Fujiwara, Y. et al. Practical and innate carbon-hydrogen functionalization of heterocycles. *Nature* 492, 95-9 (2012), incorporated herein by reference). This chemistry was originally developed for difluoromethylation of unsaturated compounds (U.S. Pat. No. 9,464,087, incorporated herein by reference). See also, U.S. Pat Nos. 9,447,164, 9,657,295, and 9,334,328, each of which is incorporated herein by reference in their entireties.

Thus, the application of this novel chemistry to nucleic acid molecules (e.g., RNA) enables the exploration of functional groups that will greatly increase the stability of long mRNAs in vivo for therapeutic purposes. Also contemplated is use of this chemistry for addition of fluorescent groups directly to RNA that could be used for in vivo monitoring of RNA localization and trafficking for research purposes. Therefore, the application of this chemistry to the RNA field has immense economic potential.

As discussed herein, the modified nucleic acid molecules can be prepared from readily available starting materials using general methods and procedures. It is understood that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The reactions of the methods described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The reactions of the methods described herein can be carried out in suitable solvents, which can be readily selected by one skilled in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The modified nucleic acid molecules and the proteins translated from the modified nucleic acid molecules described herein can be used as therapeutic agents. For example, a modified nucleic acid molecule described herein can be administered to a subject, wherein the modified nucleic acid molecule is translated in vivo to produce a therapeutic peptide in the subject. Accordingly, provided herein are compositions, methods, kits, and reagents for treatment or prevention of disease or conditions in humans and other mammals. The active therapeutic agents of the present disclosure include modified nucleic acid molecules, cells containing modified nucleic acid molecules or polypeptides translated from the modified nucleic acid molecules, polypeptides translated from modified nucleic acid molecules, and cells contacted with cells containing modified nucleic acid molecules or polypeptides translated from the modified nucleic acid molecules.

Also provided are methods of inducing translation of a recombinant polypeptide in a cell population using the modified nucleic acid molecules described herein. Such translation can be in vivo, ex vivo, in culture, or in vitro. The cell population is contacted with an effective amount of a composition containing a nucleic acid molecule that has at least one nucleobase modification, and a translatable region encoding the recombinant polypeptide. The population is contacted under conditions such that the nucleic acid molecule is localized into one or more cells of the cell population and the recombinant polypeptide is translated in the cell from the nucleic acid molecule.

An effective amount of the composition is provided based, at least in part, on the target tissue, target cell type, means of administration, physical characteristics of the nucleic acid molecule (e.g., size, and extent of modified nucleobases), and other determinants. In general, an effective amount of the composition provides efficient protein production in the cell, preferably more efficient than a composition containing a corresponding unmodified nucleic acid molecule. Increased efficiency may be demonstrated by increased cell transfection (i.e., the percentage of cells transfected with the nucleic acid molecule), increased protein translation from the nucleic acid molecule, decreased nucleic acid degradation (as demonstrated, e.g., by increased duration of protein translation from a modified nucleic acid molecule), or reduced innate immune response of the host cell.

Thus, aspects of the present disclosure are directed to methods of inducing in vivo translation of a recombinant polypeptide in a mammalian subject in need thereof. Therein, an effective amount of a composition containing a nucleic acid molecule that has at least one nucleobase modification and a translatable region encoding the recombinant polypeptide is administered to the subject using the delivery methods described herein. The nucleic acid molecule is provided in an amount and under other conditions such that the nucleic acid molecule is localized into a cell of the subject and the recombinant polypeptide is translated in the cell from the nucleic acid molecule. The cell in which the nucleic acid molecule is localized, or the tissue in which the cell is present, may be targeted with one or more than one rounds of nucleic acid administration. In various embodiments, the administered modified nucleic acid directs production of one or more recombinant polypeptides that provide a functional activity which is substantially absent in the cell in which the recombinant polypeptide is translated. For example, the missing functional activity may be enzymatic, structural, or gene regulatory in nature.

In various embodiments, the administered modified nucleic acid molecule directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. Alternatively, the recombinant polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid molecule, a carbohydrate, or a small molecule toxin.

The methods of the present disclosure therefore enhance nucleic acid delivery into a cell population, in vivo, ex vivo, or in culture. For example, a cell culture containing a plurality of host cells (e.g., eukaryotic cells such as yeast or mammalian cells) is contacted with a composition that contains a modified nucleic acid molecule having at least one nucleobase modification and, optionally, a translatable region. The composition also generally contains a transfection reagent or other compound that increases the efficiency of nucleic acid uptake into the host cells. The modified nucleic acid molecule exhibits enhanced retention in the cell population, relative to a corresponding unmodified nucleic acid molecule. The retention of the modified nucleic acid molecule is greater than the retention of the unmodified nucleic acid. In some embodiments, it is at least about 50%, 75%, 90%, 95%, 100%, 150%, 200% or more than 200% greater than the retention of the unmodified nucleic acid molecule. Such retention advantage may be achieved by one round of transfection with the enhanced nucleic acid or may be obtained following repeated rounds of transfection.

The following examples are intended to illustrate but not limit the invention.

EXAMPLE 1

Materials and Methods

Direct modification of nucleic acids with zinc sulfinate salts—This protocol results in the direct modification of nucleic acids with a moiety on the zinc sulfinate salt. The zinc sulfinate salts exemplified herein are zinc trifluoromethanesulfinate (TFMS) and zinc bis[(phenylsulfonyl)methanesulfinate] (PSMS). Nucleic acid modification with a zinc sulfinate salt results in a modification on the Hoogsteen edge of the nucleobase. In the case of adenine, it may additionally modify the Watson-Crick face. TMFS adds a trifluoromethyl modification and PSMS adds a phenylsulfonylmethyl modification.

Nucleic acid molecules—The "O.i. RNA" is a large (127 kDa), 388-nucleotides long group II intron RNA from the bacterium *Oceanobacillus iheyensis*, while "Pli. RNA" is another large (203 kDa), group II intron RNA 622-nucleotides long from the brown algae *Pylaiella littoralis*. "Unst-DNA" is a 20-nucleotide DNA of the sequence CAGAATGCTTAACGTCCGGT (SEQ ID NO: 1). "Unst-RNA" is a 20-nucleotide RNA of the sequence CAGAAUGCUUAACGUCCGGU (SEQ ID NO: 2).

Before starting the modification protocol, the RNA was prepared in 50 mM MES pH 6.5 (optionally 10 mM $MgCl_2$). The DNA was prepared in water or in 10 mM Tris HCl pH 7.5 and 0.1 mM EDTA. The following reaction components were added together (final concentrations): RNA or DNA at 1 mg/mL, 10 mM zinc sulfinate salt, 50 mM MES pH 6.5, 10 mM $MgCl_2$ and water (minus the volume of 70% tert-butyl hydroperoxide (TBHP) added later).

The reaction tube was placed on ice for at least two minutes prior to the addition of TBHP. TBHP was added to the reaction at a final concentration of approximately 15 mM. The reaction tube was kept on ice after TBHP had been added for at least two minutes. The reaction tube was then moved to the lab bench to stay at room temperature (22° C.) or to a 37° C. water bath for 24 hours.

The reaction was stopped by filtering out TBHP and salts from the nucleic acid with buffer exchange on centrifugal filters with a 30 kDa or 50 kDa molecular weight cut off (MWCO). These centrifugal filters are used for large RNAs like the O.i. group II intron. The solution used in the buffer exchange was 50 mM MES pH 6.5 or 50 mM MES pH 6.5 and 10 mM $MgCl_2$. To purify the 20-mer DNA and RNA oligos Mini Quick Spin RNA Columns or Mini Quick Spin Oligo Columns (Roche) and ethanol precipitation was used.

Copper(I)-catalyzed azide alkyne cycloaddition (CuAAC) click chemistry for modification of nucleic acids—There are two sequential steps undertaken to label nucleic acids with any alkyne-modified molecule. In the first step the nucleic acid was labeled with an azide linker, which can then react with an alkyne-containing molecule in the second step. The result of the second step is a nucleic acid labeled with any alkyne-containing molecule. This is significant because there are countless numbers of diverse alkyne-modified molecules commercially available. The diversity and ever-climbing numbers of alkyne-modified molecules available are due to the popularity of CuAAC click chemistry.

Before starting the DAAS modification protocol, the RNA was prepared in 50 mM MES pH 6.5, 10 mM $MgCl_2$ buffer. The plasmid DNA was in water. The first step reactions contain 10 mM sodium (difluoroalkylazido)sulfinate (DAAS), 50 mM MES pH 6.5, 10 mM $MgCl_2$, 4.6 mM $ZnCl_2$, 1 mg/mL nucleic acid, and water to the final volume (minus that of TBHP). The reaction tube is placed on ice for at least two minutes prior to the addition of TBHP.

70% TBHP (aqueous) was added to the reaction at a final concentration of approximately 15 mM. The reaction tube was kept on ice for at least two minutes after TBHP addition. The reaction tube was then moved to the lab bench to stay at room temperature (22° C.) for 24 hours. The first step reaction was stopped either by buffer exchange with centrifugal filters or by purification with Mini Quick Spin Columns (Roche) and ethanol precipitation.

Large nucleic acids used centrifugal filters with a 30 kDa MWCO (Corning) or 50 kDa MWCO (Millipore) and small nucleic acids (20-mer oligos) were purified with columns and ethanol precipitation. The solution used in the buffer exchange was 50 mM MES pH 6.5 and 10 mM $MgCl_2$.

The second step is the CuAAC click chemistry reaction where the DAAS-labeled nucleic acid combines with the alkyne-modified compound of interest. In these experiments the alkyne compound was Fluor-488 Alkyne. Each fluorophore reaction contained 1 uM Fluor 488-Alkyne (concentrations as low as 15 nM also worked), 20% DMSO, 6 mM THPTA, 6 mM sodium ascorbate, 3 mM $CuSO_4$ and the difluoroalkylazido-modified nucleic acid at a final concentration of 1 mg/mL. The reaction was placed in a 37° C. water bath for 30 minutes.

For large nucleic acids, the reaction was stopped by applying the sample to a 100 kDa MWCO column and purifying by buffer exchange with 50 mM MES at pH 6.5 and 10 mM $MgCl_2$ buffer. Small nucleic acids were purified with Mini Quick Spin Columns and ethanol precipitation and resuspended in water for mass spectrometry analysis.

The following MS data confirms that the TFMS, PSMS, DAAS and click chemistry reactions modify intact nucleic acids as expected. One to four modifications per molecule were observed, which is a low to moderate range of modification for a 20-nucleotide molecule. The degree of modification can be increased with a second addition of the sulfinate salt and TBHP after 24 hours. The degree of modification may also be decreased to no more than one modification per molecule using more limited amounts of the sulfinate salt and TBHP and shorter reaction times.

EXAMPLE 2

Electrospray Ionization Mass Spectrometry (ESI-MS) Data on Modified Ribonucleosides The following samples are O.i. RNA modified with a zinc sulfinate salt and then digested into nucleotides and dephosphorylated. The enzymes used for this were nuclease P1 and shrimp alkaline phosphatase (rSAP). The modification status of the ribonucleosides were next analyzed with electrospray ionization mass spectrometry (ESI-MS) in positive ion mode. A Waters I-Class HPLC was used with a Waters BEH C18 column (2.1×55 mm, 1.7 μm, 130 Å) and a gradient of 114 mM hexafluoroisopropanol and 14 mM triethylamine in water (A) and acetonitrile (B) (0.3 mL/min, 10-90% B over 10 minutes) at 60° C.

Figure 8A:
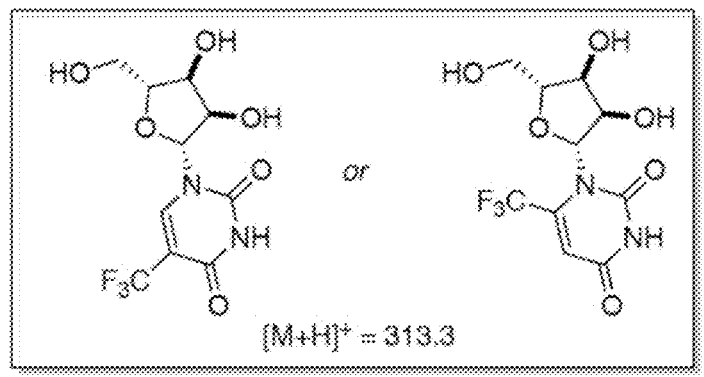
FIGS. 8A and 8B are pictorial diagrams showing trifluoromethyl-modified uridine (FIG. 8A) and trifluoromethyl-modified adenosine (FIG. 8B).
Figure 8B:
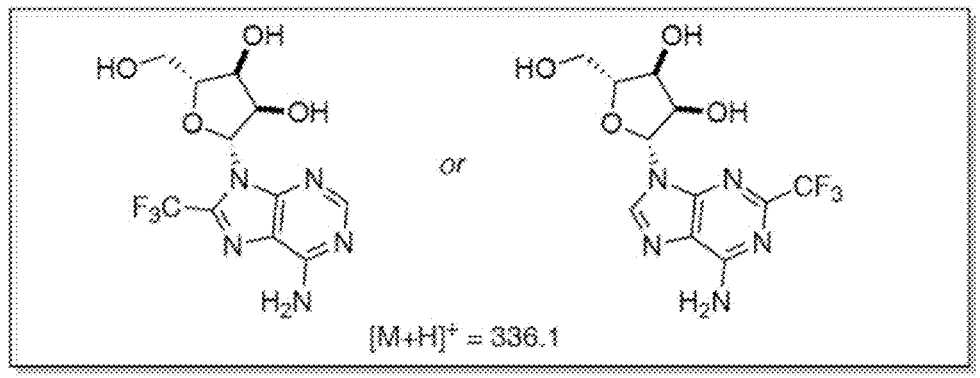

TFMS-modified ribonucleosides MS results—This sample is O.i. RNA treated with TFMS and digested into nucleosides for analysis with ESI-MS. The first four ions shown in Table 1 are unmodified uridine (m/z 245.1), unmodified cytidine (m/z 244.4), unmodified adenosine (m/z 268.3) and unmodified guanosine (m/z 284.7). The last two ions in Table 1 are trifluoromethyl-modified uridine (m/z 313.3) (FIG. 8A) and trifluoromethyl-modified adenosine (m/z 336.1) (FIG. 8B). These results show that the Hoogsteen edge of uridine and adenosine are directly modified with TFMS using the instant methodology. A fraction of the adenosine nucleosides may be modified on the Watson-Crick face instead of on the Hoogsteen edge. However, the Watson-Crick face is more likely to be engaged in hydrogen bonding, thus is correspondingly less likely to be modified.

TABLE 1

TFMS-modified ribonucleosides (O.i. RNA)

| RT | Area | Height | Base peak (m/z) |
|---|---|---|---|
| 0.137 | 2112868 | 5137211 | 245.1 |
| 0.157 | 6363241 | 7815000 | 244.4 |
| 0.187 | 2574640 | 4858544 | 268.3 |
| 0.229 | 2331267 | 5195827 | 284.7 |
| 0.907 | 1015378 | 5056582 | 313.3 |
| 1.103 | 809909 | 1158284 | 336.1 |

Figure 9C:
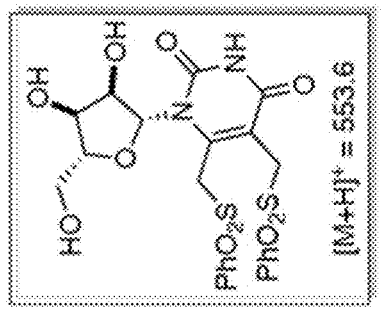
FIGS. 9A-9C are pictorial diagrams showing phenylsulfonylmethyl-modified uridine (FIG. 9A), phenylsulfonylmethyl-modified cytidine (FIG. 9B), and di-(phenylsulfonylmethyl)-modified uridine (FIG. 9C).
Figure 9B:
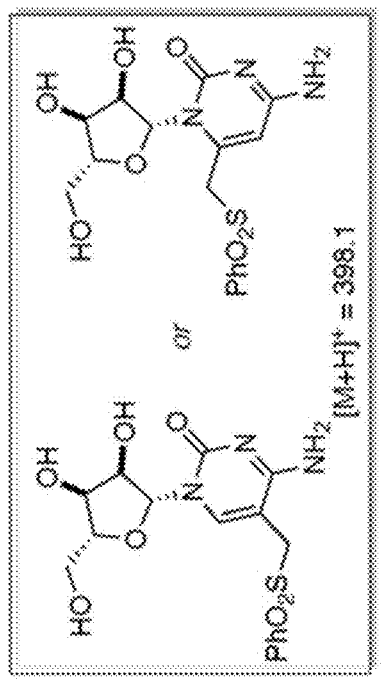
Figure 9A:
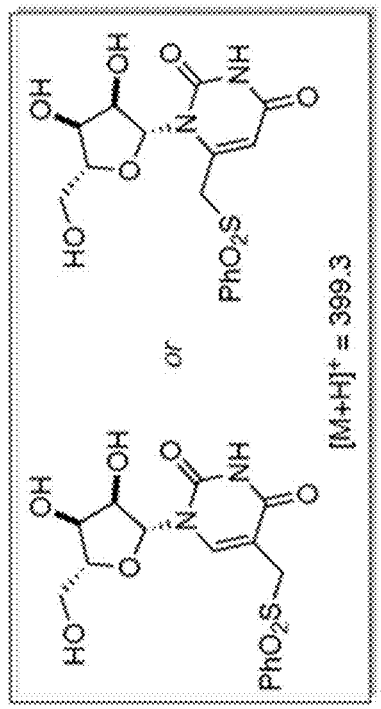

PSMS-modified ribonucleosides MS results—In this experiment, O.i. RNA is treated with PSMS and digested into nucleosides for analysis with ESI-MS. The first four ions shown in Table 2 are unmodified uridine (m/z 245.1), unmodified cytidine (m/z 244.4), unmodified adenosine (m/z 268.3) and unmodified guanosine (m/z 284.7). The last three ions in Table 2 are phenylsulfonylmethyl-modified uridine (m/z 399.3) (FIG. 9A), phenylsulfonylmethyl-modified cytidine (m/z 398.1) (FIG. 9B) and di-(phenylsulfonylmethyl)-modified uridine (m/z 553.6) (FIG. 9C). These results show that the Hoogsteen edge of uridine and cytidine are directly modified with PSMS using the instant methodology.

TABLE 2

PSMS-modified ribonucleosides (O.i. RNA)

| RT | Area | Height | Base peak (m/z) |
|---|---|---|---|
| 0.137 | 1608713 | 4025726 | 245.1 |
| 0.156 | 6256465 | 8113748 | 244.4 |
| 0.188 | 3835943 | 5035473 | 268.3 |
| 0.229 | 2976422 | 4544566 | 284.7 |
| 1.043 | 633470 | 1306317 | 399.3 |
| 1.267 | 310251 | 1237492 | 398.1 |
| 1.844 | 210334 | 1051670 | 553.6 |

Figure 10B:
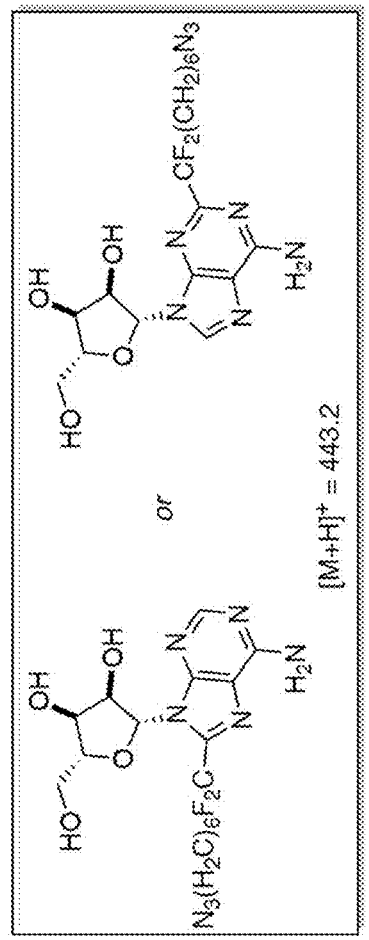
FIGS. 10A-10C are pictorial diagrams showing difluoroalkyazido-modified cytidine (FIG. 10A), difluoroalkyazido-modified adenosine (FIG. 10B), and difluoroalkyazido-modified guanosine (FIG. 10C).
Figure 10A:
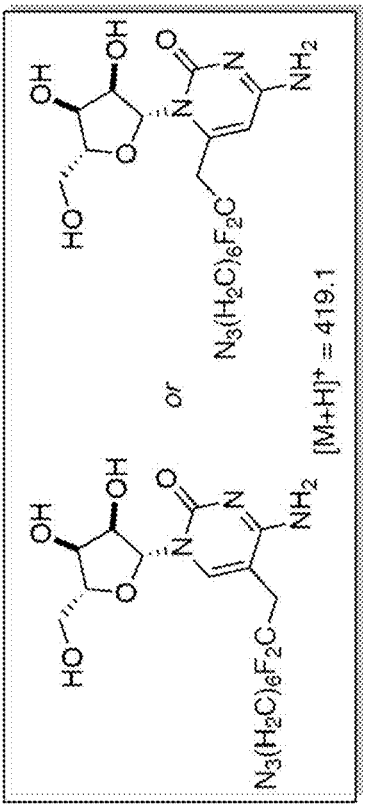
Figure 10C:
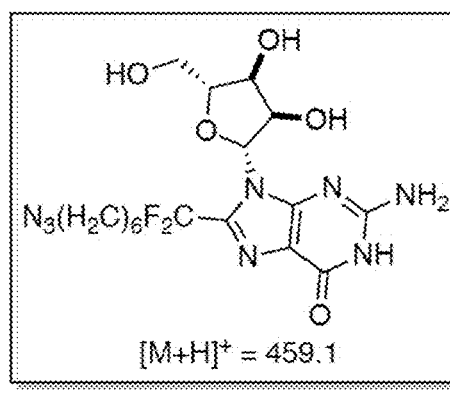

DAAS-modified ribonucleosides MS results—In this experiment, O.i. RNA is treated with DAAS and digested into nucleosides for analysis with ESI-MS. The first four ions in Table 3 are unmodified uridine (m/z 245.1), unmodified cytidine (m/z 244.4), unmodified adenosine (m/z 268.3) and unmodified guanosine (m/z 284.7). The last three ions in Table 3 are difluoroalkylazido-modified cytidine (m/z 419.1) (FIG. 10A), difluoroalkylazido-modified adenosine (m/z 443.2) (FIG. 10B) and difluoroalkylazido-modified guanosine (m/z 459.1) (FIG. 10C). These results show that the Hoogsteen edge of guanosine, cytidine and adenosine are directly modified with DAAS using the instant methodology. A fraction of the adenosine nucleosides may be modified on the Watson-Crick face instead of on the Hoogsteen edge. However, the Watson-Crick face is more likely to be engaged in hydrogen bonding, thus is correspondingly less likely to be modified.

TABLE 3

DAAS-modified ribonucleosides (O.i. RNA)

| RT | Area | Height | Base peak (m/z) |
|---|---|---|---|
| 0.137 | 1852277 | 5331495 | 245.1 |
| 0.157 | 5893378 | 7253147 | 244.4 |
| 0.184 | 3378605 | 4858644 | 268.3 |
| 0.224 | 2970156 | 3878491 | 284.7 |
| 1.102 | 231698 | 1158493 | 419.1 |
| 1.203 | 312345 | 1598323 | 443.2 |
| 1.379 | 291994 | 1427850 | 459.1 |

EXAMPLE 3

ESI-MS Data on Modified 20-Nucleotide Oligos

The modification status of each 20-nucleotide oligo was analyzed with ESI-MS in positive ion mode. A Waters I-Class HPLC was used with a Waters BEH C18 column (2.1×55 mm, 1.7 μm, 130 Å) and a gradient of 114 mM hexafluoroisopropanol and 14 mM triethylamine in water (A) and methanol (B) (0.3 mL/min, 10-26% B over 10 minutes) at 60° C.

TFMS-modified Unst-DNA MS results—The first ion shown in Table 4 is unmodified Unst-DNA (m/z 6118.11). The second and third ions are Unst-DNA with trifluoromethyl modifications: the second ion has one modification (m/z 6185.32) and the third ion has two modifications (m/z 6253.44).

TABLE 4

TFMS-modified Unst-DNA

| RT | Area | Base peak (m/z) |
|---|---|---|
| 3.05 | 217100 | 6118.11 |
| 4.22 | 88840 | 6185.32 |
| 5.01 | 79324 | 6253.44 |

PSMS-modified Unst-DNA—The first ion shown in Table 5 is unmodified Unst-DNA (m/z 6118.11) and the second ion is Unst-DNA with two phenylsulfonylmethyl modifications (m/z 6426.01).

TABLE 5

PSMS-modified Unst-DNA

| RT | Area | Base peak (m/z) |
|---|---|---|
| 3.05 | 2752000 | 6118.11 |
| 4.36 | 842300 | 6426.01 |

DAAS-modified Unst-DNA—The first ion shown in Table 6 is unmodified Unst-DNA (m/z 6118.11) and the second ion is Unst-DNA with one difluoroalkylazido modification (m/z 6293.31).

TABLE 6

DAAS-modified Unst-DNA

| RT | Area | Base peak (m/z) |
|---|---|---|
| 3.05 | 2148000 | 6118.11 |
| 5.68 | 89240 | 6293.31 |

Fluor 488-modified Unst-DNA—The first ion shown in Table 7 is unmodified Unst-DNA (m/z 6118.11). The second and third ions are Unst-DNA with Fluor 488 and difluoroalkylazido modifications: the second ion has three Fluor 488 modifications (m/z 8404.43) and the third ion has three Fluor 488 modifications and one difluoroalkylazido modification (m/z 8580.56).

TABLE 7

Fluor 488-modified Unst-DNA

| RT | Area | Base peak (m/z) |
|---|---|---|
| 2.25 | 13800000 | 6118.11 |
| 5.63 | 761700 | 8404.43 |
| 5.82 | 663400 | 8580.56 |

DAAS-modified Unst-RNA—The first ion shown in Table 8 is unmodified Unst-RNA (m/z 6367.89) and the second ion is Unst-RNA with one difluoroalkylazido modification (m/z 6542.7).

TABLE 8

DAAS-modified Unst-RNA

| RT | Area | Base peak (m/z) |
|---|---|---|
| 1.76 | 23120000 | 6367.89 |
| 4.37 | 998700 | 6542.7 |

Fluor 488-modified Unst-RNA—The first ion shown in Table 9 is unmodified Unst-RNA (m/z 6367.89). The second and third ions are Unst-RNA with Fluor 488 and difluoroalkylazido modifications: the second ion has three Fluor 488 modifications (m/z 8654.87) and the third ion has one Fluor 488 modification and one difluoroalkylazido modification (m/z 7305.32).

TABLE 9

Fluor 488-modified Unst-RNA

| RT | Area | Base peak (m/z) |
|---|---|---|
| 1.76 | 22590000 | 6367.89 |
| 4.87 | 861900 | 8654.87 |
| 5.71 | 733400 | 7305.32 |

EXAMPLE 4

Fluorine-19 (F-19) NMR Data

Figure 11:
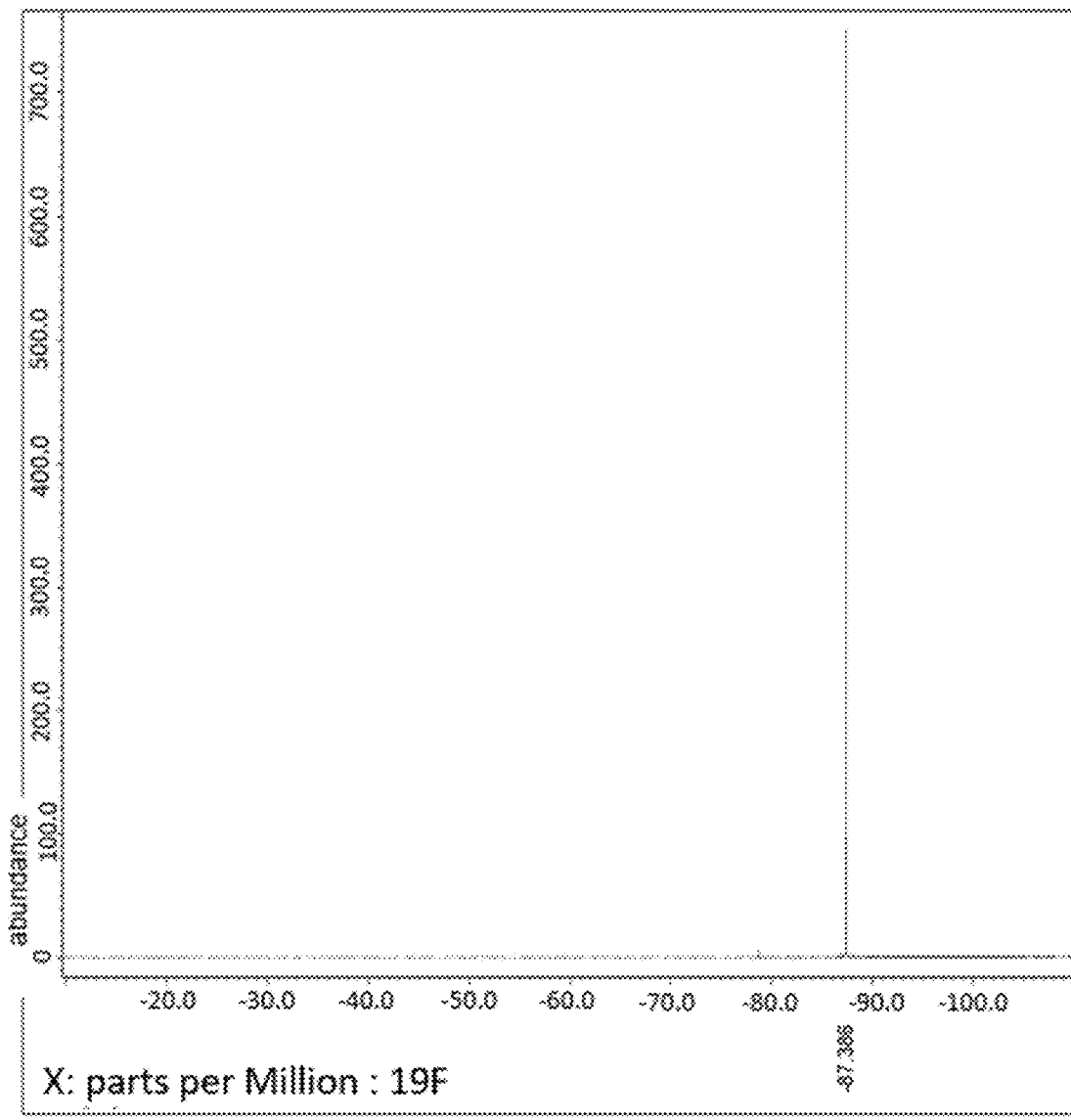
FIG. 11 is a graphical diagram showing the fluorine 19 (F-19) NMR spectrum for zinc trifluoromethylsulfinate (TFMS) salt.

The fluorine-19 NMR spectrum for zinc trifluoromethylsulfinate (TFMS) salt is shown in FIG. 11. TFMS was at a concentration of 45 mM in a solution of water and 10% deuterium oxide ($D_2O$) and the data was recorded on a 300 MHz Bruker. The chemical shift is a single peak at −87.38 ppm. This chemical shift is characteristic of TFMS, which has a published F-19 NMR chemical shift of −85.7 ppm (DMSO-d6 solvent) (Fujiwara et al., 2012).

Figure 12:
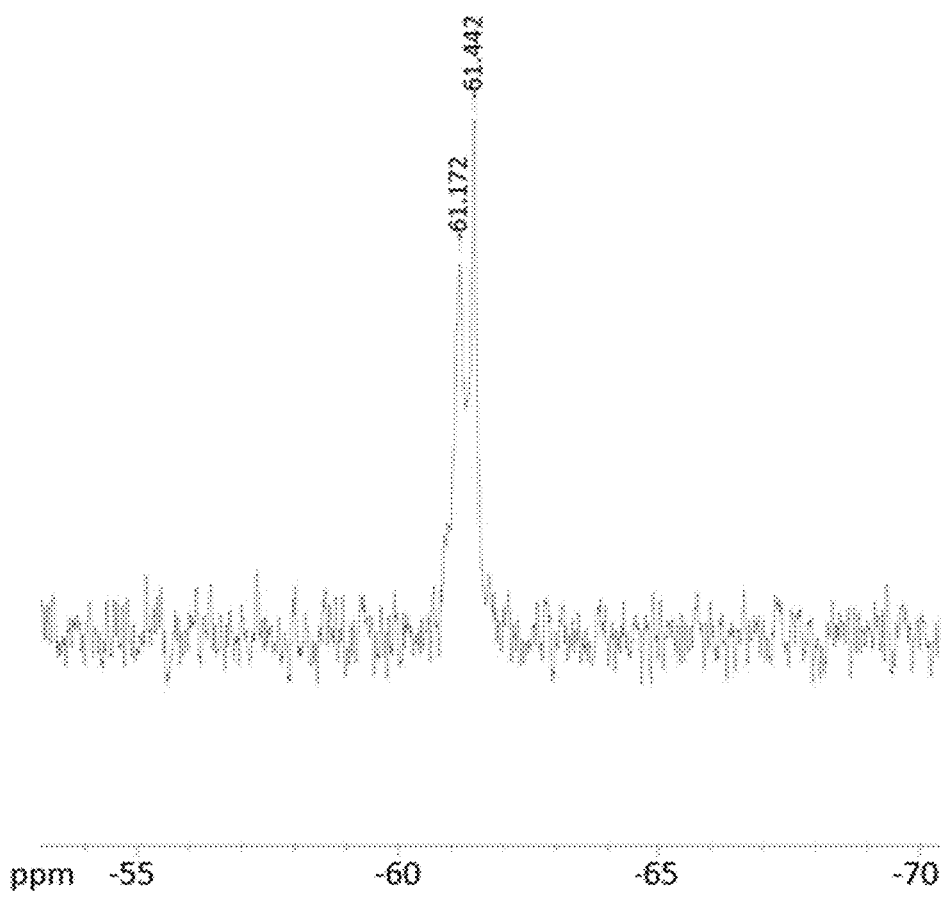
FIG. 12 is a graphical diagram showing the fluorine 19 (F-19) NMR spectrum for trifluoromethyl-modified *Oceanobacillus iheyensis* (O.i.) RNA.

FIG. 12 provides the fluorine-19 NMR spectrum for trifluoromethyl-modified O.i. RNA. The sample was at a final concentration of 10.6 mg/mL RNA in a solution of 50 mM MES pH 6.5, 10 mM $MgCl_2$ and 10% $D_2O$. The RNA chemical shifts are −61.2 and −61.4 ppm in 10% $D_2O$ and the data was captured with a 300 MHz Bruker. The fluorine-19 NMR signal for this RNA supports the assertion that the intact TFMS-modified O.i. RNA contains fluorine. The chemical shifts are also distinguishably different from the TFMS F-19 NMR signal (−87.4 ppm). Additionally, the observed chemical shifts are similar to the reference chemical shifts for 2-(trifluoromethyl)pyridyl and caffeine-$CF_3$. 2-(trifluoromethyl)pyridyl has a chemical shift of −62 ppm in $CDCl_3$ solvent (Pretsch et al., 2009) and is similar in structure to a trifluoromethyl-modified uracil or trifluoromethyl-modified cytosine. Caffeine-$CF_3$ has a reported chemical shift of −62.7 ppm in $CDCl_3$ solvent (Ji et al., 2011).

Figure 13:
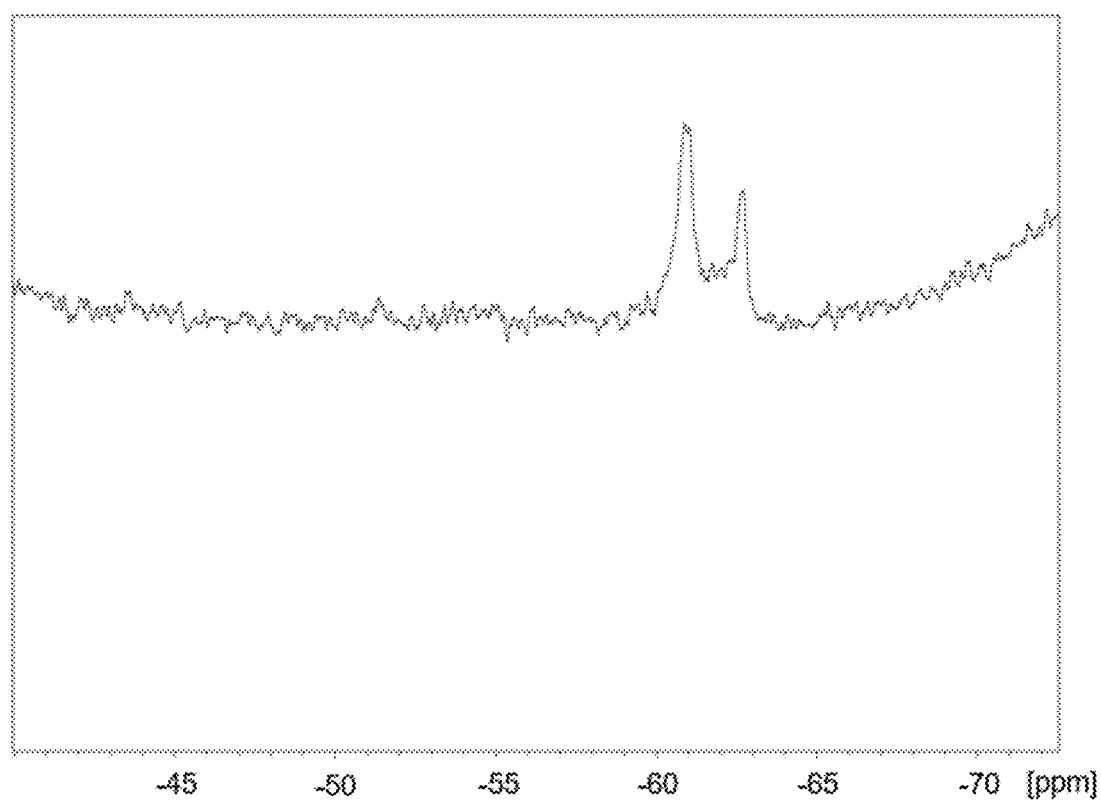
FIG. 13 is a graphical diagram showing the fluorine 19 (F-19) NMR spectrum for trifluoromethyl-modified *Pylaiella littoralis* (Pli.) RNA.

FIG. 13 shows the fluorine-19 NMR spectrum for trifluoromethyl-modified Pli. RNA (Pli. RNA is much larger than O.i. RNA). The RNA was at a concentration of 10.42 mg/mL in a solution of 40 mM MES pH 6.5, 10 mM $MgCl_2$ and 10% $D_2O$. The RNA chemical shifts are −60.9 and −62.7 ppm in 10% $D_2O$ and the data was captured with a 300 MHz Bruker. Pli. RNA's F-19 NMR chemical shifts are very different from that of TFMS (−87.4 ppm) and much less different from the O.i. RNA chemical shifts (−61.2 and −61.4 ppm). The simple fact that a fluorine-19 signal was detected supports the assertion that the intact TFMS-modified Pli. RNA contains fluorine modifications since unmodified RNAs do not contain fluorine. Additionally, the observed Pli. RNA chemical shifts are similar to the reference chemical shifts for 2-(trifluoromethyl)pyridyl and caffeine-$CF_3$. 2-(trifluoromethyl)pyridyl has a chemical shift of −62 ppm in $CDCl_3$ solvent (Pretsch et al., 2009) and is similar in structure to a trifluoromethyl-modified uracil or trifluoromethyl-modified cytosine. Caffeine-$CF_3$ has a reported chemical shift of −62.7 ppm in $CDCl_3$ solvent (Ji et al., 2011).

EXAMPLE 5

Gel Data

FIGS. 14A and 14B are images of the same 4% acrylamide denaturing PAGE gel prepared with different imaging techniques. FIG. 14A is the scan using a GE Typhoon Fluorescent Image Analyzer Scanner with a 473 nm excitation beam and the LPB filter. FIG. 14B is the UV-illuminated gel stained with ethidium bromide. Lane 1 contains the control: unmodified O.i. RNA, treated without DAAS in the first reaction step and treated the same as the experimental sample in the second step of the CuAAC reactions. Lane 2 contains the fluorophore-labeled O.i. RNA, which is modified in the first step with DAAS and then reacted with Fluor 488-Alkyne in the second step. The fluorescent band shown in lane 2 of FIG. 14A shows successful labeling of the RNA with Fluor 488.

Figure 15:
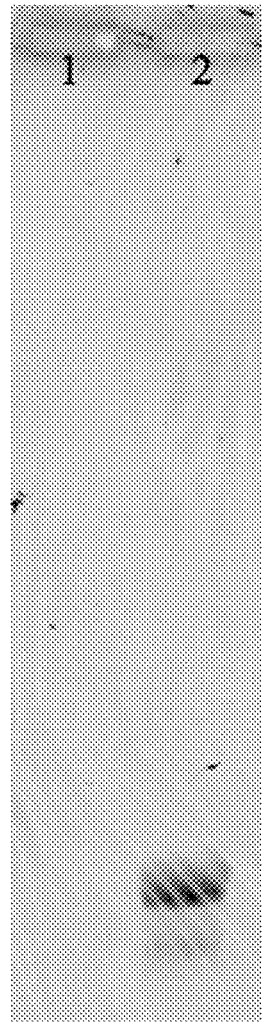
FIG. 15 is a pictorial diagram showing detection of fluorescence from Fluor 488-labeled plasmid DNA. The experimental lane shows the presence of a fluorescent DNA band indicating that the DNA was successfully labeled by the fluorophore Fluor 488. The control lane contains DNA with no prior azide addition that was incubated with the dye and shows no visible fluorescence.

FIG. 15 shows an agarose gel scanned using a GE Typhoon Fluorescent Image Analyzer Scanner with a 473 nm excitation beam and the LPB filter. Lane 1 contained the control: unmodified O.i. plasmid DNA, which was treated without DAAS in the first reaction step and treated the same as the experimental sample in the second step of the CuAAC reactions. Lane 2 contained the fluorophore-labeled O.i. plasmid DNA, which is modified in the first step with DAAS and then reacted with Fluor 488-Alkyne in the second step. The fluorescent band in lane 2 confirms successful tagging of the DNA with Fluor 488.

The following references are hereby incorporated by reference in their entireties.

1. Kariko et al. Incorporation of pseudouridine into mRNA yields superior nonimmunogenic vector with increased translational capacity and biological stability. Mol Ther. 2008; 16(11):1833-40. Epub 2008/09/18. doi: 10.1038/mt.2008.200. PubMed PMID: 18797453; PMCID: PMC2775451.

2. Andries et al. N(1)-methylpseudouridine-incorporated mRNA outperforms pseudouridine-incorporated mRNA by providing enhanced protein expression and reduced immunogenicity in mammalian cell lines and mice. J Control Release. 2015; 217:337-44. Epub 2015/09/03. doi: 10.1016/j.jconrel.2015.08.051. PubMed PMID: 26342664.

3. Claborn et al. Nusinersen: A Treatment for Spinal Muscular Atrophy. Ann Pharmacother. 2018: 1060028018789956. Epub 2018/07/01. doi: 10.1177/1060028018789956. PubMed PMID: 30008228.

4. Groen et al. Advances in therapy for spinal muscular atrophy: promises and challenges. Nat Rev Neurol. 2018; 14(4):214-24. Epub 2018/02/09. doi: 10.1038/nrneurol.2018.4. PubMed PMID: 29422644.

5. Wu et al. T7 RNA Polymerase Discriminates Correct and Incorrect Nucleoside Triphosphates by Free Energy. Biophys J. 2018; 114(8):1755-61. doi: 10.1016/j.bpj.2018.02.033. PubMed PMID: 29694856; PMCID: PMC5937113.

6. Zubradt et al. DMS-MaPseq for genome-wide or targeted RNA structure probing in vivo. Nat Methods. 2017; 14(1):75-82. Epub 2016/11/07. doi: 10.1038/nmeth.4057. PubMed PMID: 27819661; PMCID: PMC5508988.

7. Ziehler and Engelke. Probing RNA structure with chemical reagents and enzymes. Curr Protoc Nucleic Acid Chem. 2001; Chapter 6:Unit 6.1. doi: 10.1002/0471142700.nc0601s00. PubMed PMID: 18428862; PMCID: PMC3746551.

8. Frye et al. RNA modifications modulate gene expression during development. Science. 2018; 361(6409):1346-9. doi: 10.1126/science.aau1646. PubMed PMID: 30262497; PMCID: PMC6436390.

9. Sahin et al. mRNA-based therapeutics—developing a new class of drugs. Nat Rev Drug Discov. 2014; 13(10): 759-80. Epub 2014/09/23. doi: 10.1038/nrd4278. PubMed PMID: 25233993.

10. Fujiwara, et al. (2012). Practical and innate carbon-hydrogen functionalization of heterocycles. Nature. 2012; 492(7427):95-9. Epub 2012/11/28. doi: 10.1038/nature11680. PubMed PMID: 23201691; PMCID: PMC3518649.

11. Yue et al. RNA N6-methyladenosine methylation in post-transcriptional gene expression regulation. Genes Dev. 2015; 29(13):1343-55. doi: 10.1101/gad.262766.115. PubMed PMID: 26159994; PMCID: PMC4511210.

12. Mortimer and Weeks. A fast-acting reagent for accurate analysis of RNA secondary and tertiary structure by SHAPE chemistry. J Am Chem Soc. 2007; 129(14):4144-5. doi: 10.1021/ja0704028. PubMed PMID: 17367143.

13. Wilkinson et al. Selective 2'-hydroxyl acylation analyzed by primer extension (SHAPE): quantitative RNA structure analysis at single nucleotide resolution. Nat Protoc. 2006; 1(3):1610-6. doi: 10.1038/nprot.2006.249. PubMed PMID: 17406453.

14. Sharma et al. On the role of Hoogsteen:Hoogsteen interactions in RNA: ab initio investigations of structures and energies. RNA. 2010; 16(5):942-57. Epub 2010/03/30. doi: 10.1261/rna.1919010. PubMed PMID: 20354152; PMCID: PMC2856888.

15. Pretsch, et al. Structure Determination of Organic Compounds: Tables of Spectral Data, Fourth Edition edn. ed2009.

16. Toor et al. Crystal structure of a self-spliced group II intron. Science. 2008. 320: 77-82.

17. Robart et al. Crystal structure of a eukaryotic group II intron lariat. Nature. 2014; 514(7521):193-7. Epub 2014/09/26. doi: 10.1038/nature13790. PubMed PMID: 25252982; PMCID: Pmc4197185.

18. Ban et al. The complete atomic structure of the large ribosomal subunit at 2.4 A resolution. Science. 2000; 289 (5481):905-20. PubMed PMID: 10937989.

19. Keating and Pyle. Semiautomated model building for RNA crystallography using a directed rotameric approach. Proc Natl Acad Sci USA. 2010; 107(18):8177-82. doi: 0911888107 [pii] 10.1073/pnas.0911888107. PubMed PMID: 20404211; PMCID: PMC2889552.

20. Wadley et al. Evaluating and learning from RNA pseudotorsional space: quantitative validation of a reduced representation for RNA structure. J Mol Biol. 2007; 372(4): 942-57. doi: 10.1016/j.jmb.2007.06.058. PubMed PMID: 17707400; PMCID: PMC2720064.

21. Weil et al. Making the message clear: visualizing mRNA localization. Trends Cell Biol. 2010; 20(7):380-90. Epub 2010/05/03. doi: 10.1016/j.tcb.2010.03.006. PubMed PMID: 20444605; PMCID: PMC2902723.

22. Zhou et al. Bioconjugation by native chemical tagging of C—H bonds. J Am Chem Soc. 2013;135(35):12994-7. Epub 2013/08/22. doi: 10.1021/ja407739y. PubMed PMID: 23957305; PMCID: PMC3812917.

23. Kolb et al. Click Chemistry: Diverse Chemical Function from a Few Good Reactions. Angew Chem Int Ed Engl. 2001; 40(11):2004-21. PubMed PMID: 11433435.

24. Rostovtsev et al. A stepwise huisgen cycloaddition process: copper(I)-catalyzed regioselective "ligation" of azides and terminal alkynes. Angew Chem Int Ed Engl. 2002; 41(14):2596-9. doi: 10.1002/1521-3773(20020715) 41:14<2596:AID-ANIE2596>3.0.CO;2-4. PubMed PMID: 12203546.

25. Arun et al. Differentiation of mammary tumors and reduction in metastasis upon Malat1 lncRNA loss. Genes Dev. 2016; 30(1):34-51. Epub 2015/12/23. doi: 10.1101/gad.270959.115. PubMed PMID: 26701265; PMCID: PMC4701977.

26. Wu et al. Long Noncoding RNA MALAT1: Insights into its Biogenesis and Implications in Human Disease. Curr Pharm Des. 2015; 21(34):5017-28. PubMed PMID: 26205289.

27. Tripathi et al. The nuclear-retained noncoding RNA MALAT1 regulates alternative splicing by modulating SR splicing factor phosphorylation. Mol Cell. 2010; 39(6):925-38. doi: 10.1016/j.molcel.2010.08.011. PubMed PMID: 20797886; PMCID: PMC4158944.

28. Guzikowski et al. Stress-induced mRNP granules: Form and function of processing bodies and stress granules. Wiley Interdiscip Rev RNA. 2019; 10(3):e1524. Epub 2019/02/21. doi: 10.1002/wrna.1524. PubMed PMID: 30793528; PMCID: PMC6500494.

29. Biscans et al. Diverse lipid conjugates for functional extra-hepatic siRNA delivery in vivo. Nucleic Acids Res. 2018. Epub 2018/12/14. doi: 10.1093/nar/gky1239. PubMed PMID: 30544191; PMCID: PMC6379722.

30. McHugh et al. The Xist lncRNA interacts directly with SHARP to silence transcription through HDAC3. Nature. 2015; 521(7551):232-6. Epub 2015/04/27. doi: 10.1038/nature14443. PubMed PMID: 25915022; PMCID: PMC4516396.

31. Moritz and Wahle. Simple methods for the 3' biotinylation of RNA. RNA. 2014; 20(3):421-7. Epub 2014/01/21. doi: 10.1261/rna.042986.113. PubMed PMID: 24448448; PMCID: PMC3923135.

32. Kariko et al. Generating the optimal mRNA for therapy: HPLC purification eliminates immune activation and improves translation of nucleoside-modified, protein-encoding mRNA. Nucleic Acids Res. 2011; 39(21):e142. Epub 2011/09/06. doi: 10.1093/nar/gkr695. PubMed PMID: 21890902; PMCID: PMC3241667.

33. Herbert et al. Reactivity and Specificity of RNase T 1, RNase A, and RNase H toward Oligonucleotides of RNA Containing 8-Oxo-7,8-dihydroguanosine. Biochemistry. 2018; 50:2971-83.

34. Ji, et al. (2011). Innate C—H trifluoromethylation of heterocycles. Proc Natl Acad Sci USA 108, 14411-14415.

Although the invention has been described with reference to the above examples, it will be understood that modifications and variations are encompassed within the spirit and scope of the invention. Accordingly, the invention is limited only by the following claims.

What is claimed is:

1. A method of modifying a nucleic acid molecule comprising:
   (a) contacting the nucleic acid molecule with an azide linker under conditions sufficient to add an azide group to a nucleobase of the nucleic acid molecule, thereby forming an azide-labeled nucleic acid molecule; and
   (b) contacting the azide-labeled nucleic acid molecule with an alkyne-labeled molecule comprising an R group in the presence of a copper catalyst under conditions sufficient for covalent attachment of the R group to the nucleobase, thereby forming a modified nucleic acid molecule.

2. The method of claim 1, wherein the azide linker is a sulfinate salt comprising an azide group.

3. The method of claim 1, wherein the nucleobase is selected from the group consisting of adenine, deoxyadenine, guanine, deoxyguanine, 5-methyluracil, thymine, uracil, deoxyuracil, cytosine, deoxycytosine, and any combination thereof.

4. The method of claim 1, wherein the nucleic acid molecule is selected from the group consisting of RNA, DNA, TNA, GNA, PNA, LNA, and hybrids thereof.

5. The method of claim 1, wherein the R group comprises biotin.

6. The method of claim 1, wherein the alkyne-labeled molecule is an alkyne-labeled lipid.

7. The method of claim 5, further comprising transfecting the biotinylated nucleic acid molecule into cells under conditions sufficient to allow for interaction with cellular protein cofactors, and thereafter, purifying the nucleic acid molecule with a streptavidin column to detect bound cellular proteins.

8. A method of screening for nucleobase modifications that reduce cleavage of a nucleic acid molecule by a nuclease, the method comprising:
   (a) contacting the nucleic acid molecule with an azide linker under conditions sufficient to add an azide group to a nucleobase of the nucleic acid molecule, thereby forming an azide-labeled nucleic acid molecule;
   (b) contacting the azide-labeled nucleic acid molecule with an alkyne-labeled molecule comprising an R group in the presence of a copper catalyst under conditions sufficient for covalent attachment of the R group to the nucleobase, thereby forming a modified nucleic acid molecule; and
   (c) monitoring degradation of the modified nucleic acid molecule over time in the presence of a nuclease, wherein decreased degradation in the presence of the nuclease, as compared to degradation in the presence of the nuclease of the nucleic acid molecule prior to modification is indicative of a R group that stabilizes the nucleic acid molecule.

9. The method of claim 8, further comprising repeating steps (a)-(c) using an alkyne-labeled molecule that comprises a different R group.

10. The method of claim 8, wherein the azide linker is a sulfinate salt comprising an azide group.

* * * * *